United States Patent
Fukagai et al.

(10) Patent No.: US 7,636,624 B2
(45) Date of Patent: Dec. 22, 2009

(54) DIAGNOSTIC METHOD AND CONTROL APPARATUS FOR GAS SENSOR

(75) Inventors: Reina Fukagai, Aichi (JP); Norikazu Ieda, Ichinomiya (JP); Masahiro Tanaka, Kasugai (JP); Hiroshi Inagaki, Komaki (JP); Masaki Hirata, Hamamatsu (JP); Takahiro Suzuki, Hamamatsu (JP)

(73) Assignees: NGK Spark Plug Co., Ltd., Nagoya-shi, Aichi (JP); Suzuki Motor Corporation, Hamamatsu-shi, Shizuoka (JP)

( * ) Notice: Subject to any disclaimer, the term of this patent is extended or adjusted under 35 U.S.C. 154(b) by 152 days.

(21) Appl. No.: 12/033,614

(22) Filed: Feb. 19, 2008

(65) Prior Publication Data

US 2008/0196489 A1 Aug. 21, 2008

(30) Foreign Application Priority Data

Feb. 21, 2007 (JP) .............................. 2007-040940
Jun. 25, 2007 (JP) .............................. 2007-166612

(51) Int. Cl.
 *G06F 19/00* (2006.01)
 *G01N 27/404* (2006.01)
(52) U.S. Cl. .................... 701/34; 73/1.06; 73/23.31; 73/23.32; 701/29; 701/35; 340/514; 340/632
(58) Field of Classification Search ................. 60/285; 73/1.06, 3.31, 2.32, 3.33, 3.34; 204/421, 204/424; 340/514, 632; 701/29, 34, 35; 702/116
See application file for complete search history.

(56) References Cited

U.S. PATENT DOCUMENTS

| | | | | |
|---|---|---|---|---|
| 5,020,499 A | * | 6/1991 | Kojima et al. | 123/479 |
| 5,461,569 A | * | 10/1995 | Hara et al. | 701/101 |
| 5,491,631 A | * | 2/1996 | Shirane et al. | 701/35 |
| 5,685,284 A | * | 11/1997 | Nakamichi | 123/688 |
| 5,927,260 A | * | 7/1999 | Kishimoto et al. | 123/688 |
| 6,136,169 A | * | 10/2000 | Okamoto | 204/401 |
| 6,157,310 A | * | 12/2000 | Milne et al. | 340/679 |
| 6,818,120 B2 | * | 11/2004 | Nakamichi et al. | 205/784.5 |
| 6,836,722 B2 | * | 12/2004 | Yook | 701/114 |
| 6,912,887 B2 | * | 7/2005 | Ikeda | 73/1.06 |
| 6,976,382 B2 | * | 12/2005 | Kadowaki et al. | 73/1.06 |
| 6,996,974 B2 | * | 2/2006 | Anilovich et al. | 60/285 |

(Continued)

FOREIGN PATENT DOCUMENTS

JP  60-192847 A  10/1985

(Continued)

*Primary Examiner*—David A. Rogers
(74) *Attorney, Agent, or Firm*—Flynn, Thiel, Boutell & Tanis, P.C.

(57) ABSTRACT

A gas sensor diagnostic method (or apparatus) is arranged to periodically obtain sensor output values of a gas sensor such as an oxygen sensor for an internal combustion engine, and to determine local extreme values from the sensor output values obtained during a period of interruption of fuel supply to the engine. Moreover, the local extreme values are compared with a first predetermined threshold level. When the number of the local extreme values reaches a predetermined first number, a diagnosis is performed to determine whether the gas sensor is in an improper condition or not, in accordance with results of the comparison of the local extreme values with the first threshold level.

16 Claims, 8 Drawing Sheets

U.S. PATENT DOCUMENTS

| | | | |
|---|---|---|---|
| 7,536,244 B2* | 5/2009 | Kunihiro et al. | 701/34 |
| 2002/0175086 A1* | 11/2002 | Nakamichi et al. | 205/775 |
| 2003/0225505 A1* | 12/2003 | Yook | 701/114 |
| 2004/0100271 A1* | 5/2004 | Ikeda | 324/514 |
| 2004/0130442 A1* | 7/2004 | Breed et al. | 340/443 |
| 2006/0025897 A1* | 2/2006 | Shostak et al. | 701/1 |
| 2007/0273540 A1 | 11/2007 | Inoue et al. | |
| 2007/0276580 A1 | 11/2007 | Toda et al. | |

FOREIGN PATENT DOCUMENTS

| | | |
|---|---|---|
| JP | 60-233343 A | 11/1985 |
| JP | 2003-185626 A | 7/2003 |

* cited by examiner

DIAGNOSTIC METHOD AND CONTROL APPARATUS FOR GAS SENSOR

BACKGROUND OF THE INVENTION

The present invention relates to gas sensor diagnosing method for examining whether a gas sensor disposed in an exhaust passage of an internal combustion engine is in an improper condition or not, and/or gas sensor control or diagnostic apparatus for such a gas sensor.

A three-way catalyst is widely used in internal combustion engines for motor vehicles and other applications, to purify CO, HC and NOx contained in exhaust gas mixture. Furthermore, in order to improve the efficiency of the purification, there is provided a feedback air-fuel ratio control system including a gas sensor disposed in the exhaust passage of the engine, for sensing the oxygen concentration in the exhaust gases, and a controller for controlling the mixture ratio or air-fuel ratio toward the theoretical air-fuel ratio by regulating a fuel supply quantity, such as a fuel injection quantity, to the engine in accordance with the sensed oxygen concentration. Recently, the feedback air-fuel ratio control system often employs, as the gas sensor, a wide-range or full-range air-fuel ratio sensor varying the sensor output linearly in accordance with the oxygen concentration in the exhaust gases, in order to improve the accuracy of the feedback control.

Since the sensing element of the gas sensor is exposed directly to the exhaust gases in the exhaust passage, a poisoning component, such as phosphorous, in the exhaust gases can adhere to porous portions through which the exhaust gas mixture is introduced into the inside of the sensing element. If the amount of adhesion of the poisoning component increases too much, the sensitivity of the gas sensor (the gain of the sensor output) with respect to a change in the concentration of the specified component might decrease. Moreover, if cracks are formed in the sensing element, the sensitivity of the gas sensor might increase too much beyond the normal level. If the sensitivity of the gas sensor is not normal, the feedback air-fuel ratio control system might become unable to control the air-fuel ratio normally, and the three-way catalyst might become unable to purify the harmful components sufficiently.

Therefore, published Japanese Patent Applications, Publication Numbers S60-233343 and S60-192847 propose a gas sensor diagnostic method for detecting degradation of a gas sensor. While the fuel supply to an internal combustion engine is being interrupted, the air of the atmosphere is supplied to the gas sensor, so that a value of the sensor output is predictable. By utilizing the fuel supply interruption period, the diagnostic method determines the existence or nonexistence of a malfunction in the feedback air-fuel ratio control system inclusive of the gas sensor, by comparing a gas sensor output value obtained a predetermined time after a start of the fuel supply interruption, with a predetermined reference value. The feedback air-fuel ratio control system can perform this diagnostic method with its own controller without the need for a special sensor.

SUMMARY OF THE INVENTION

However, the sensor output of the gas sensor may have a plurality of peaks in its waveform, and may be affected by noise. Therefore, the diagnosis tends to be inaccurate and unstable when the diagnosis is configured to compare a sensor output value directly with a reference value, and to judge that there occurs a malfunction if a single sensor output value becomes greater than a reference value.

Therefore, it is an object of the present invention to provide gas sensor diagnostic or control method and/or apparatus suitable for detecting an improper condition of a gas sensor accurately.

According to one aspect of the invention, a gas sensor diagnostic method of diagnosing an improper condition of a gas sensor for producing a gas sensor output representing a concentration of a specified gas component in an exhaust gas mixture of an internal combustion engine, comprises: a sensor output obtaining step of obtaining sensor output values of the gas sensor output at regular time intervals of a predetermined obtaining period; an interruption detecting step of detecting a fuel supply interruption to the engine; an extremum determining step of determining local extreme values each of which is an extremum in a series of sensor output values obtained consecutively by the sensor output obtaining step during a fuel supply interruption period during which the fuel supply interruption is detected by the interruption detecting step; an extremum comparing step of comparing the local extreme values with a first predetermined threshold level; and a diagnosing step of determining whether the gas sensor is in the improper condition or not, in accordance with results of the comparison of the local extreme values with the first threshold level when the number of the local extreme values obtained from the gas sensor output becomes equal to a predetermined first number. The local extreme value of the gas sensor output may be a local maximal value (a greatest value among values within a given neighborhood, to form an upward peak in a waveform) or may be a local minimal value (a smallest value among values within a given neighborhood, to form a downward valley in the waveform).

According to another aspect of the present invention, a gas sensor control apparatus to diagnose an improper condition of a gas sensor comprises: a sensor output obtaining section to obtain sensor output values of the gas sensor output at regular time intervals of a predetermined obtaining period; an interruption detecting section to detect a fuel supply interruption to the engine; an extremum determining section to determine local extreme values of the sensor output from a series of sensor output values obtained consecutively during a fuel supply interruption period; an extremum comparing section to compare the local extreme values with a first predetermined threshold level; and a diagnosing section to determine whether the gas sensor is in the improper condition or not, in accordance with results of the comparison of the local extreme values with the first threshold level when the number of the local extreme values obtained from the gas sensor output becomes equal to a predetermined first number.

According to still another aspect of the present invention, a gas sensor control apparatus comprises: means for determining local extreme values of a sensor output of a gas sensor, from sensor output values obtained consecutively during interruption of fuel supply to an internal combustion engine; means for comparing the local extreme values with a first predetermined threshold level; and means for determining whether the gas sensor is in the improper condition or not, in accordance with results of the comparison of the local extreme values with the first threshold level when the number of the local extreme values obtained from the gas sensor output becomes equal to a predetermined first number. The gas sensor control apparatus may further comprise: means for periodically obtaining sensor output values ($V(n)$) of the gas sensor output; and means for detecting the interruption of the fuel supply to the engine.

According to still another aspect of the present invention, a gas sensor control apparatus comprises: a processor to determine local extreme values of a sensor output of a gas sensor, from sensor output values obtained consecutively during interruption of fuel supply to an internal combustion engine; to compare the local extreme values with a first predetermined threshold level; and to determine whether the gas sensor is in the improper condition or not, in accordance with results of the comparison of the local extreme values with the first threshold level when the number of the local extreme values obtained from the gas sensor output becomes equal to a predetermined number.

According to still another aspect of the invention, a gas sensor diagnostic method comprises: a first method element (such as a step) of determining local extreme values each of which is an extremum in a series of sensor output values of a sensor output of a gas sensor obtained consecutively during interruption of fuel supply to an internal combustion engine; a second method element of comparing the local extreme values with a first predetermined threshold level; and a third method element of examine results of the comparison of the local extreme values with the first threshold level to determine the improper/proper condition of the gas sensor, in accordance with the results of the comparison when the number of the local extreme values obtained from the gas sensor output becomes equal to a predetermined first number.

DETAILED DESCRIPTION OF THE INVENTION

Figure 1:
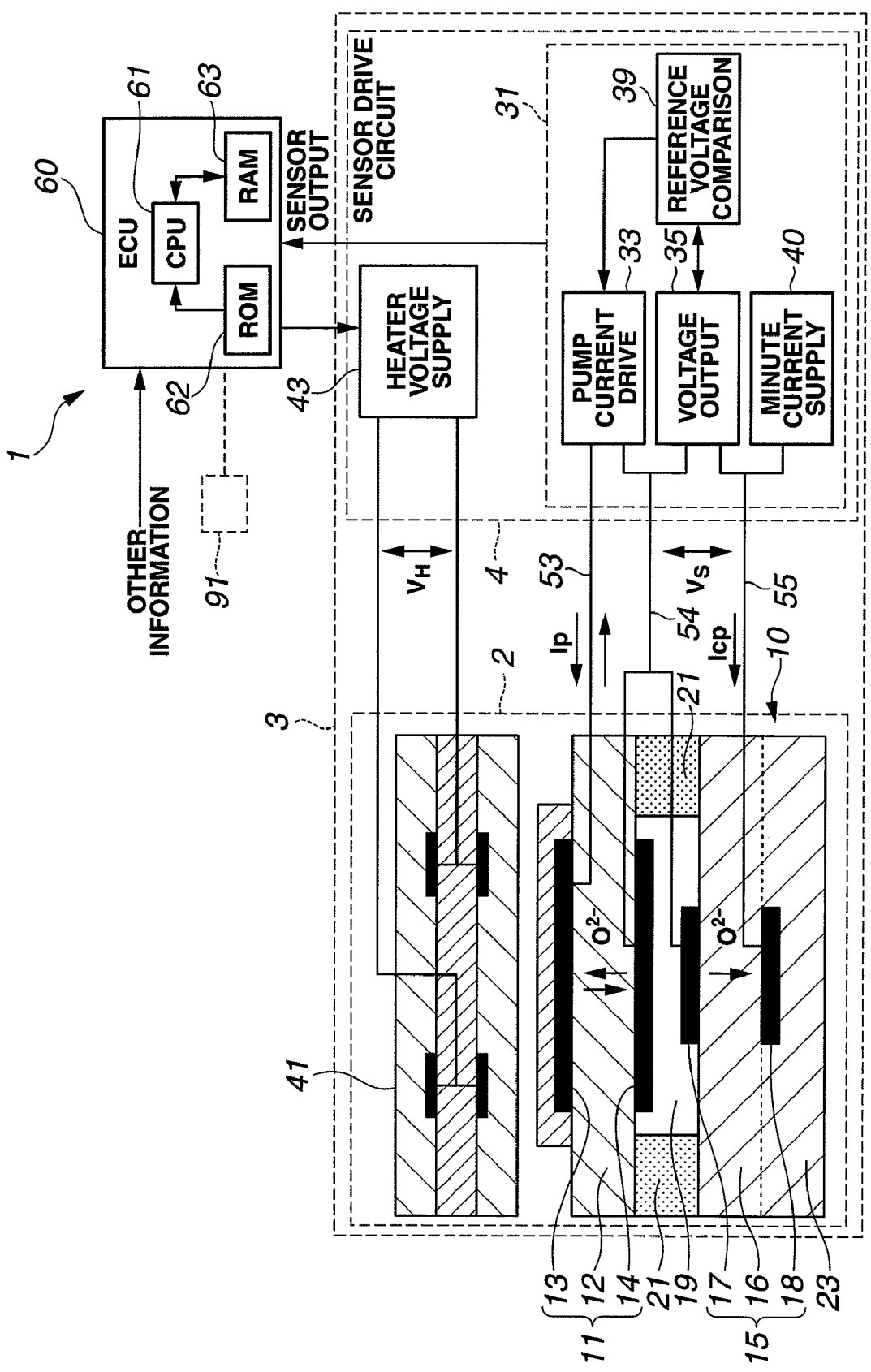
FIG. 1 is a view schematically showing the structure of a gas sensor system including a gas sensor control device 1 and a gas sensor unit 3, according to a first embodiment (and a second embodiment) of the present invention.

FIGS. 1~6 show a gas sensor diagnosis or diagnostic method for determining whether a gas sensor is in an abnormal state or not, and a gas sensor system, according to a first embodiment of the present invention. As shown in FIG. 1, the gas sensor system includes a gas sensor unit 3 and a gas sensor control device or controller 1. In the example shown in FIG. 1, gas sensor unit 3 employs a wide-range (or full-range) air-fuel ratio sensing element 10 (hereinafter referred simply as sensing element 10) capable of sensing the oxygen concentration in a wide (or full) range of the air-fuel ratio from the rich region to the lean region across the theoretical air-fuel ratio. In this example, the gas sensor system is arranged to sense the concentration of oxygen contained in exhaust gases of an internal combustion engine for a vehicle, by using the sensor output of gas sensor unit 3, and to use, or enable the use of, the sensed oxygen concentration for the control (such as feedback control) of the air-fuel ratio of the internal combustion engine.

Gas sensor unit 3 has the structure schematically shown in FIG. 1, and produces a sensor output representing the oxygen concentration in the exhaust gas mixture of the internal combustion engine. Gas sensor unit 3 includes a gas sensor 2 which includes the sensing element 10 and a ceramic heater 41. Gas sensor unit 3 of this example further includes a sensor drive circuit 4 which includes a sensor control circuit 31 connected with sensing element 10, and a heater voltage supply circuit 43 connected with ceramic heater 41. Gas sensor unit 3 of FIG. 1 further includes three lead lines (or wires) 53, 54 and 55 for connecting sensing element 10 electrically with sensor control circuit 31. The three lead lines are: pump-side lead line 53, common lead line 54 and sensor-side lead line 55.

Gas sensor control device 1 has the structure schematically shown in FIG. 1. Gas sensor control device 1 includes an ECU (engine control unit) 60 for diagnosing gas sensor 2 and for controlling heater voltage supply circuit 43 in accordance with a sensor resistance signal supplied from sensor control circuit 31 separately. Gas sensor control device 1 may further include an output section 91 which is connected with ECU 60 and which includes at least one of a display or a warning device, for presenting the results of the diagnosing process according to this embodiment; and a communicating device for sending a signal to external equipment.

Heater voltage supply circuit 43, ECU 60 and sensor control circuit 31 start the respective operations in response to a start signal inputted from the outside at the time of a start of the internal combustion engine.

Wide-range air-fuel ratio sensing element 10 of gas sensor 2 includes a laminate of a shield layer 23, an oxygen concentration sensing cell 15, a gas sensing chamber 19 and an oxygen pumping cell 11 which are laminated in this order from bottom to top as viewed in FIG. 1.

Oxygen pumping cell 11 of sensing element 10 includes porous electrodes 13 and 14 provided, respectively, on the upper and lower sides of a solid electrolyte plate or layer 12, and performs the function of pumping oxygen ($O_2$) as a specific gas component to be monitored by gas sensor 2. Oxygen concentration sensing cell 15 of sensing element 10 includes porous electrodes 17 and 18 provided, respectively, on the upper and lower sides of a solid electrolyte plate or layer 16, and performs the function of producing an electromotive force in accordance with the oxygen concentration. Gas sensing chamber 19 is a cavity formed between the oxygen pumping cell 11 and oxygen concentration sensing cell 15, and so arranged that measurement gas to be examined is introduced into gas sensing chamber 19. The porous electrode 14 of oxygen pumping cell 11 and the porous electrode 17 of oxygen concentration sensing cell 15 are disposed so that both electrodes are exposed in gas sensing chamber 19, and both confront each other. A gas diffusion porous layer 21 for defining gas sensing chamber 19 between oxygen pumping cell 11 and oxygen concentration sensing cell 15 and for controlling the diffusion rate of the gas is disposed in a path for introducing the measurement gas to be examined, into gas sensing chamber 19. In this example, the solid electrolyte plates 12 and 16, and shield layer 23 are formed by using, as a main component of material, partially stabilized zirconia including yttria as a stabilizer in a solid solution. Porous electrodes 13, 14, 17 and 18 are made predominantly of platinum.

Shield layer 23 is disposed on the (lower) side of solid electrolyte plate or layer 16 of oxygen concentration sensing cell 15 opposite to gas sensing chamber 19 so that the solid electrolyte plate 16 is disposed between gas sensing chamber 19 on the upper side and shield layer 23 on the lower side. The porous electrode 18 disposed between shield layer 23 and oxygen concentration sensing cell 15 stores oxygen in pores in the electrode 18. The thus-accumulated oxygen serves as reference oxygen in oxygen concentration sensing cell 15. Therefore, porous electrode 18 can serve as a reference oxygen electrode.

Ceramic heater 41 of gas sensor 2 is shaped like a flat plate as shown in FIG. 1. Ceramic heater 41 is disposed on the upper side of oxygen pumping cell 11 so that ceramic heater 41 and oxygen pumping cell 11 confront each other. Ceramic heater 41 is a device for activating sensing element 10. Ceramic heater 41 receives the supply of electric power from heater voltage supply circuit 43, and controls the temperature of sensing element 10 to a predetermined temperature. Heater voltage supply circuit 43 supplies power to ceramic heater 41 under the control of ECU 60, as mentioned later.

Sensor control circuit 31 is electrically connected with sensing element 10 by the before-mentioned three lead lines 53, 54 and 55, as shown in FIG. 1, and arranged to deliver a sensor output to ECU 60. Sensor control circuit 31 is a circuit known per se. Sensor control circuit 31 includes a pump current drive circuit 33, a voltage output circuit 35, a reference voltage comparison circuit 39 and a minute current supply circuit 40.

Minute current supply circuit 40 of sensor control circuit 31 is to cause minute current Icp to flow from porous electrode 18 to porous electrode 17 of oxygen concentration sensing cell 15. By the supply of minute current Icp from minute current supply circuit 40, oxygen is drawn to porous electrode 18, which functions as an oxygen reference electrode. Voltage output circuit 35 is a circuit to sense an electromotive force Vs generated between porous electrodes 17 and 18 of oxygen concentration sensing cell 15. Reference voltage comparison circuit 39 is a comparator which holds therein a predetermined reference voltage (450 [mV] in this example); compares the electromotive force Vs sensed by voltage output circuit 35 with the reference voltage; and feeds the result of the comparison back to pump current drive circuit 33. In accordance with the result of the comparison fed back from reference voltage comparison circuit 39, the pump current drive circuit 33 controls the pump current Ip supplied to oxygen pumping cell 11.

ECU 60 of gas sensor control device 1 includes CPU 61, ROM 62 and RAM 63, as shown in FIG. 1. CPU 61 is a main component of gas sensor control device 1. Specifically, CPU 61 is configured to control heater voltage supply circuit 43 controlling the supply of electricity to ceramic heater 41. ROM 62 stores programs and data such as various set values used in the later-mentioned diagnosing process. RAM 63 is a memory that can be both read and altered (written) in normal operation. ECU 60 receives the sensor output and sensor resistance signal which are outputted from gas sensor 2 through sensor drive circuit 4. Moreover, ECU 60 receives other information such as a signal representing a condition of fuel supply to the internal combustion engine, a signal representing the on/off condition of an ignition switch, and a signal or signals representing one or more operating conditions of the engine and providing information as to whether all of various engine operating parameter conditions are met continuously for a predetermined time duration.

In the example shown in FIG. 1, the sensor control circuit 31 and heater voltage supply circuit 43 are constituent parts of gas sensor unit 3. However, it is optional to construct the gas sensor unit 3 and gas sensor control device 1 so that either or both of gas sensor control circuit 31 and heater voltage supply circuit 43 is included in gas sensor control device 1, instead of gas sensor unit 3. When, for example, gas sensor control device 1 includes both of gas sensor control circuit 31 and heater voltage supply circuit 43, and gas sensor unit 3 includes only the gas sensor 2, the output of gas sensor 2 is inputted directly to gas sensor control device 1. Thus, the sensor output of gas sensor 2 may be inputted to gas sensor control device 1, directly or through an interface or interfaces such as sensor control circuit 31.

Figure 2:
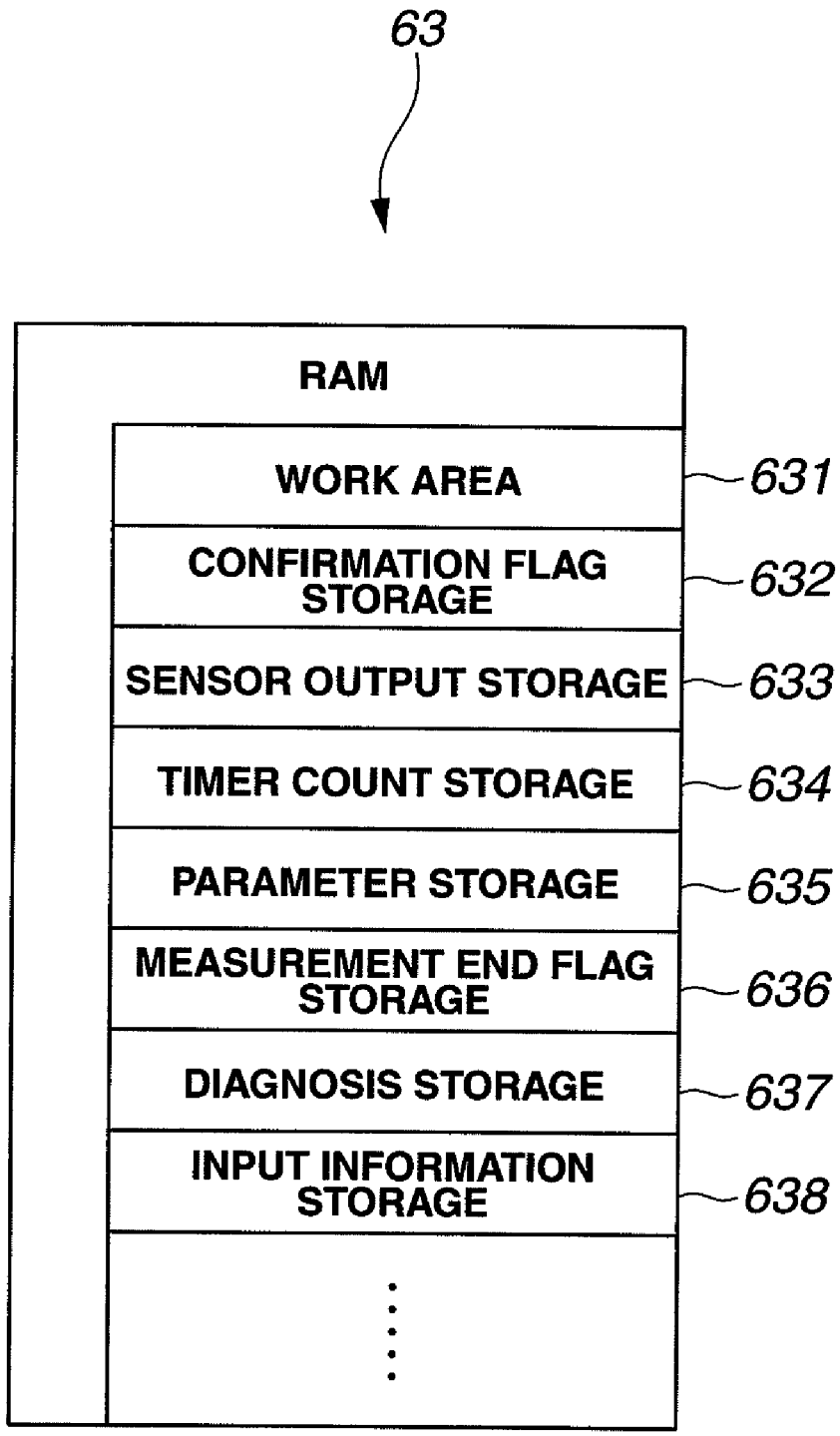
FIG. 2 is a schematic view for illustrating storage areas in RAM 63 shown in FIG. 1.

FIG. 2 schematically shows memory areas in RAM 63 of ECU 60. In the example of FIG. 2, RAM 63 includes: a work area 631 for storing various set values read from ROM 62 and the results of calculation performed by CPU 61; a confirmation flag storage area 632 for storing a confirmation flag indicating whether the engine operating parameter conditions are satisfied continuously during a predetermined time duration or not; a sensor output storage area 633 for storing one or more values of the sensor output supplied from gas sensor unit 3; a timer counter storage area 634 for storing a count to which a predetermined number is added at regular time intervals according to a timer program; a parameter storage area 635 for storing one or more diagnostic parameters used in the gas sensor diagnosing process; a measurement end flag storage area 636 for storing a measurement end flag indicating the execution of the diagnosing process; a diagnosis storage area 637 for storing the result of the diagnosing process; and an input information storage area 638 for storing input information supplied to gas sensor control device 1. RAM 63 may further include other storage areas according to the need. In this example, the diagnostic parameters stored in parameter storage area 635 for use in the diagnosing process are: a maximum which is a local maximum or local maximal value among values of the sensor output obtained at regular time intervals; a number of obtained maximum values of the sensor output; a number of obtained non-maximum values of the sensor output; a number of obtained over maximum values of the sensor output greater than an upper limit La; and a number of obtained under maximum values of the sensor output smaller than a lower limit Lb. The input information stored in input information storage area 638 includes the signal representing the condition of the fuel supply to the engine, the signal representing the on/off condition of the ignition switch and the signal representing the continuation for the predetermined time duration, or non-continuation, of fulfillment of the engine operating parameter conditions.

Gas sensor control device 1 controls heater voltage supply circuit 43 in the following manner. Sensor control circuit 31 is arranged to deliver the sensor resistance signal to ECU 60. Though not shown in FIG. 1, sensor control circuit 31 includes a sensor resistance sensing circuit which is known per se. This sensor resistance sensing circuit is arranged to supply a current of a constant value periodically to oxygen concentration sensing cell 15 from a current supply circuit provided separately from minute current supply circuit 40; to sense, as the sensor resistance signal, a potential difference produced between the porous electrodes 17 and 18 of the oxygen concentration sensing cell 15 due to the supply of the current to oxygen concentration sensing cell 15; and to supply the thus-obtained sensor resistance signal to ECU 60. ECU 60 determines the temperature Tc of sensing element 10 from the sensor resistance signal supplied from gas sensor unit 3, and delivers a heater control signal to control the voltage applied to ceramic heater 41, to heater voltage supply circuit 43. Specifically, in this example, ECU 60 performs a temperature control process to regulate the voltage VH applied to the heater in accordance with the sensor resistance signal supplied from sensor control circuit 31 so as to bring the temperature Tc of sensing element 10 closer to a normal temperature (800 [° C.], for example) higher than or equal to an activation temperature (600 [° C.], for example), and to bring the sensor resistance Rpvs of oxygen concentration sensing cell 15, toward a target resistance Rta corresponding to the normal temperature. The temperature Tc at oxygen concentration sensing cell 15 of sensing element 10 is related to the sensor resistance Rpvs, so that temperature Tc can be determined from the sensor resistance Rpvs. Consequently, the oxygen pumping cell 11 and oxygen concentration sensing cell 15 are heated above the activation temperature, and sensing element 10 is brought to an active state capable of sensing the oxygen. The temperature control process performed by ECU 60 is known per se. Since it is possible to employ, as the temperature control process, a control process disclosed in a published Japanese Patent Application Publication No. 2003-185626, further detailed explanation is omitted.

The sensor system determines the oxygen concentration in the exhaust gas mixture in accordance with the sensor output from gas sensor unit 3, and determines the air-fuel ratio in the following manner. Between porous electrodes 17 and 18 of oxygen concentration sensing cell 15, there is produced an electromotive force Vs corresponding to the oxygen concentration in gas sensing chamber 19. So as to hold this electromotive force Vs at a constant value (450 [mV], for example), oxygen (O2) is drawn into or out of gas sensing chamber 19 in sensing element 10, with oxygen pumping cell 11. In this case, the magnitude and direction of the pump current flowing through oxygen pumping cell 11 are varied in dependence on the oxygen concentration. Therefore, the gas sensor system can sense the oxygen concentration in the exhaust gases by using the sensed pumping current Ip. In the first embodiment, the voltage proportional to the magnitude of pumping current Ip is delivered, as the sensor output, from sensor control circuit 31 to gas sensor control device 1, and ECU 60 of gas sensor control device 1 determines the oxygen concentration and diagnose the gas sensor 2 by using this sensor output. Moreover, ECU 60 determines the air-fuel ratio of the engine from the sensed oxygen concentration by utilizing a relationship between the oxygen concentration in the exhaust gases and the air-fuel ratio.

Figure 3:
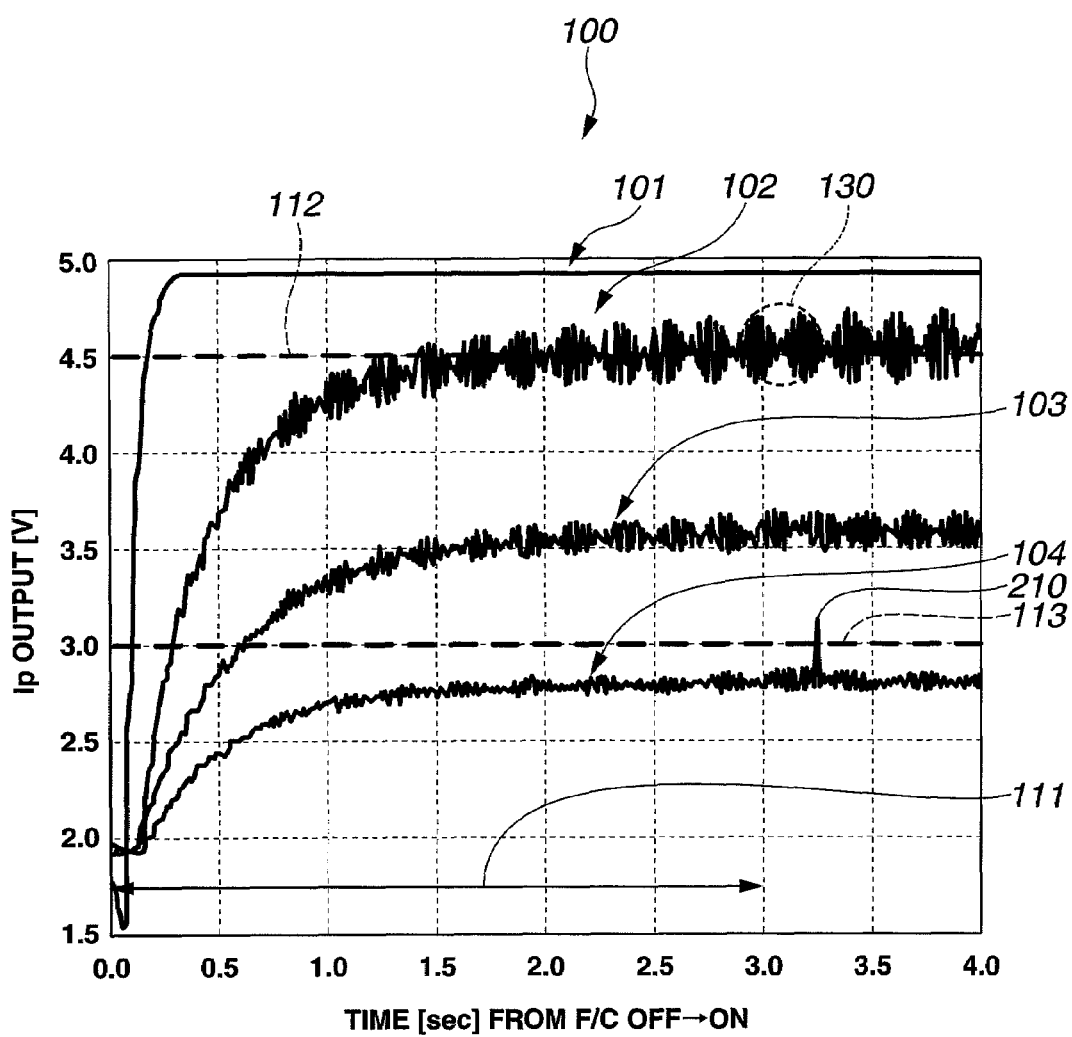
FIG. 3 is a graph showing, as an example, various waveforms of a sensor output signal outputted from gas sensor unit 3 after a start of interruption of fuel supply (F/C) to an internal combustion engine.
Figure 4:
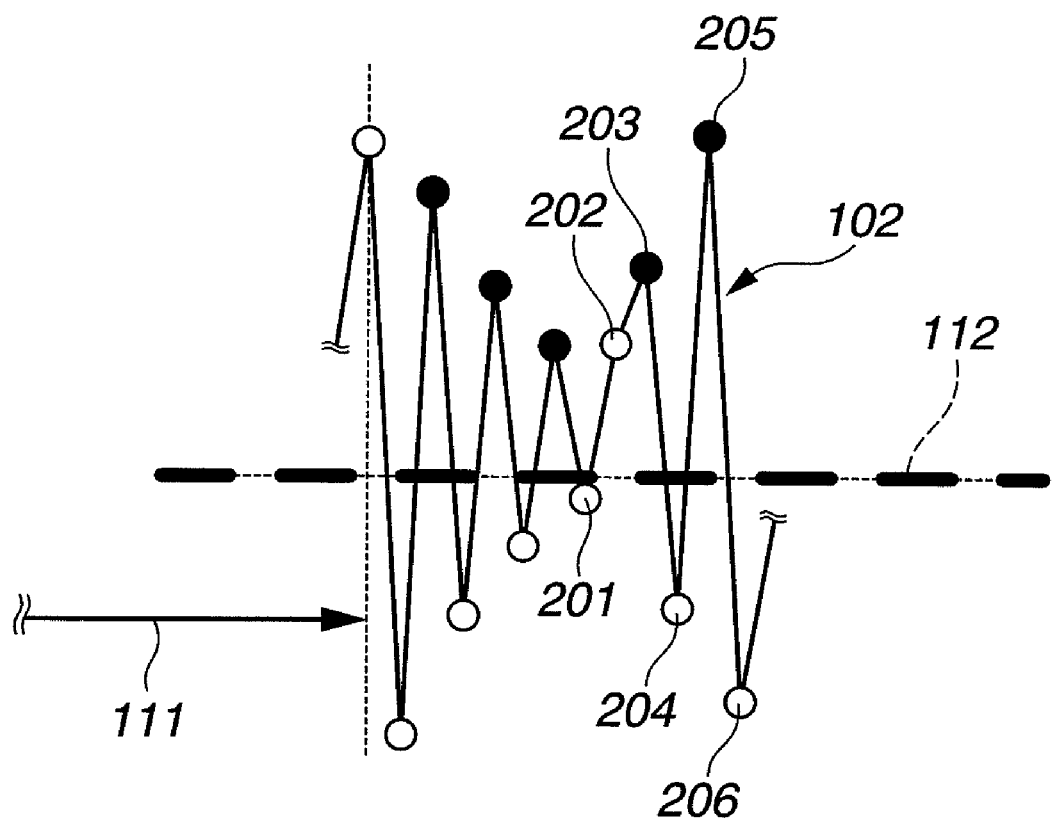
FIG. 4 is an enlarged graph showing a portion 130 enclosed by a broken line in FIG. 3.
Figure 5:
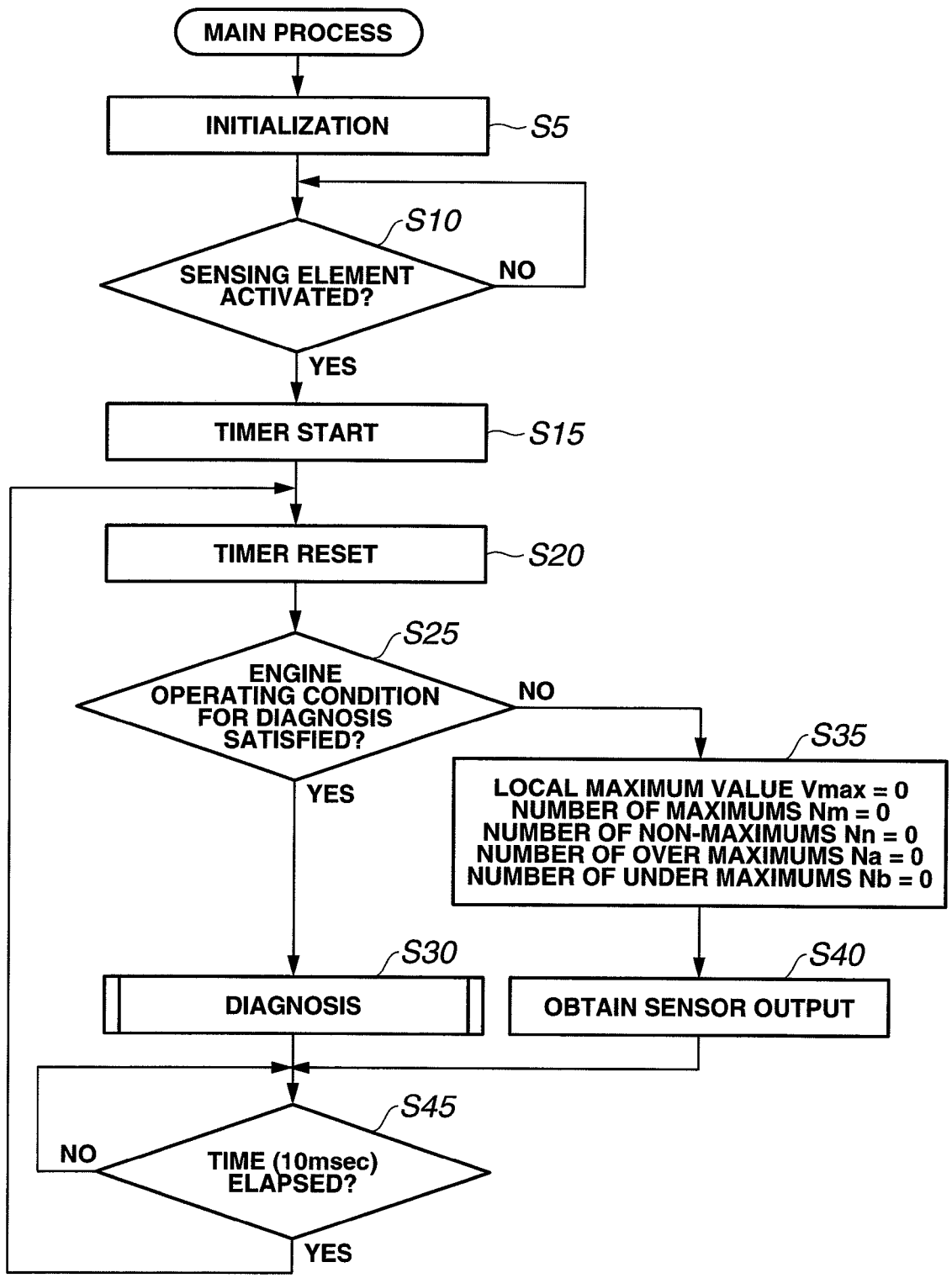
FIG. 5 is a flowchart showing a main process of a diagnostic method according to the first embodiment, for examining whether gas sensor 2 is in an improper condition or not.
Figure 6:
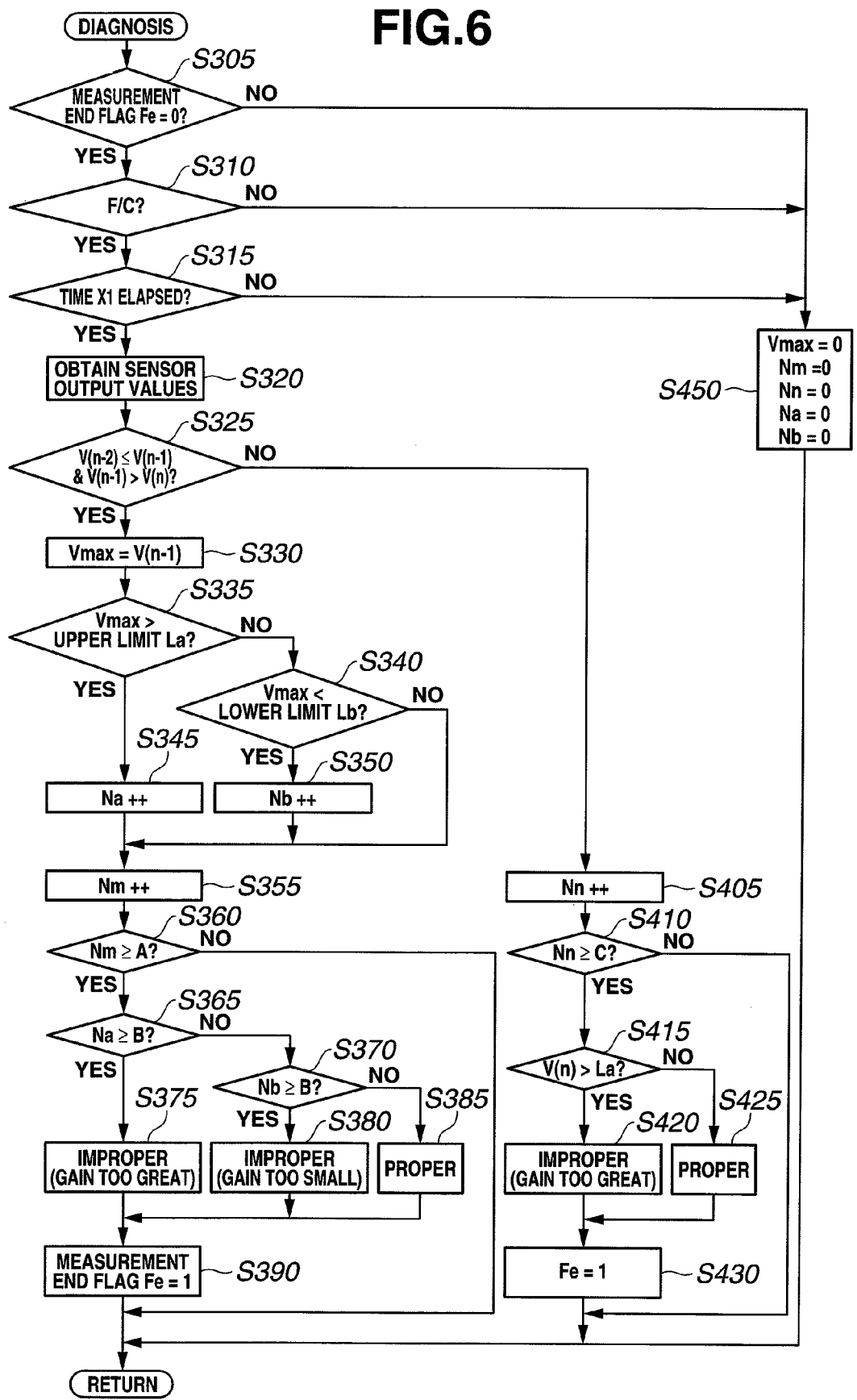
FIG. 6 is a flowchart showing a diagnostic process performed in the main process of FIG. 5, according to the first embodiment.

FIGS. 3~6 are views for illustrating a gas sensor diagnostic method of determining whether the gas sensor 2 is in an improper condition or not, in accordance with the sensor output of gas sensor 2. FIG. 3 is a graph showing, as an example, variation with time of the sensor output outputted from gas sensor unit 3 after a start of interruption (F/C) of the fuel supply to the internal combustion engine. FIG. 4 is a graph showing, on an enlarged scale, a portion 130 enclosed by a broken line in FIG. 3. FIG. 5 shows, in the form of a flowchart, a main process of the gas sensor diagnostic method. FIG. 6 shows, in the form of a flowchart, a diagnosis in the main process of FIG. 5. In this example, CPU 61 shown in FIG. 1 performs the processes of FIGS. 5 and 6 according a program stored in ROM 62, as well as other programs performed by ECU 60.

To examine whether the gas sensor 2 is in the improper condition incapable functioning properly, the diagnostic system monitors the sensor output of gas sensor 2 which varies with time as shown in FIGS. 3 and 4. A graph 100 of FIG. 3 shows four waveforms 101~104 of the sensor (output) signal of gas sensor 2 after a start of fuel supply interruption (F/C) which is interruption or stoppage of the supply of fuel to the internal combustion engine. Sensor signal waveform 101 is an example to be judged to be improper (gain too great) by the diagnostic process because the sensor output is too high with respect to the oxygen concentration in the exhaust gases (that is, the sensitivity of gas sensor 2 is too high). Waveform 102 having an approximately constant period, and a periodically varying amplitude is an example to be judged to be improper (gain too great) by the diagnostic process. Waveform 103 having an approximately constant period, and a periodically varying amplitude is an example to be judged proper by the diagnostic process. Waveform 104 having an approximately constant period and a periodically varying amplitude is an example to be judged improper (gain too small) because the sensor output is too small with respect to the oxygen concentration in the exhaust gases (the sensitivity of gas sensor 2 is too low). A portion 130 of waveform 102 is shown in the enlarged view of FIG. 4 with sensor output values 201~206 obtained after the lapse of a predetermined time interval X1 from a start of the full supply interruption (F/C) as shown by an arrow 111.

The outline of the diagnostic process according to the first embodiment is as follows. During the interruption of the fuel supply, the atmospheric air is supplied to gas sensor 2. Therefore, after the elapse of a predetermined time interval from the start of the fuel supply interruption (F/C), the sensor output of gas sensor 2 outputted from gas sensor unit 3 becomes equal to a value corresponding to the oxygen concentration of the air. If, however, gas sensor 2 is deteriorated by adhesion, to a porous portion of gas sensor 2 (such as gas diffusion porous layer 21), of a great amount of poisoning component such as phosphorous contained in the exhaust gases, cracks produced in sensing element 10 or other factors, the sensitivity of gas sensor 2 could become too low or too high with respect to variation in the oxygen concentration, and the sensor output could shift out of the expected normal range corresponding to the oxygen concentration of the air.

Therefore, the diagnostic system can determine the improper/proper condition of gas sensor 2, by using the gas sensor output after the end of a predetermined time interval from a start of the fuel supply interruption (F/C), and upper and lower limits of the normal range of the output of gas sensor 2 in the normal state. However, the sensor output outputted from gas sensor unit 3 has a waveform having a plurality of extremums, or upward and downward peaks, as shown in the examples 102~104. Therefore, the diagnosis tends to be inaccurate and instable when the diagnostic system is arranged to compare a sensor output value directly with the upper and lower limits, and to judge that there occurs a malfunction, if a single sensor output value becomes greater than the upper limit or smaller than the lower limit. Furthermore, noise could produce a peak such as a peak 210 in the waveform 104, and thereby cause misjudgment of the diagnostic system. Therefore, the diagnostic system according to the first embodiment compares extreme values, such as local maximal values and/or local minimal values, of the sensor output, with a first threshold level such as the upper and/or lower limits, and determines the improper/proper condition of gas sensor 2 in accordance with the results of the comparisons. By so doing, the diagnostic system can detect the improper condition of the gas sensor accurately even if a sensor output waveform has a plurality of extremums, or a noise is superimposed on the sensor output.

FIG. 5 shows the main process of the diagnostic method according to the first embodiment. A step S5 is a step for initialization for initializing various data and flags. In this example, at S5, CPU 61 resets a measurement end flag Fe indicating the execution or nonexecution of the diagnostic process, to zero to indicate that the diagnostic process is not yet performed, and stores the value of measurement end flag Fe in measurement end flag storage area 636 in RAM 63. Furthermore, at S5, CPU 61 clears a value of the sensor output stored in sensor output storage area 633 and the order (n) of sampling this value stored in sensor output storage area 633 together with the sensor output value. A next step S10 is for activation check for examining whether sensing element 10 is activated or not. At S10, CPU 61 examines whether sensing element 10 is heated to a temperature at which the mobility of oxygen ions is sufficiently increased, and hence sensing element 10 is in an active state capable sensing the oxygen concentration. As explained before, there is a relationship between the temperature Tc of oxygen concentration sensing cell 15 and the sensor resistance Rpvs of oxygen concentration sensing cell 15 of sensing element 10. Therefore, CPU 61 ascertain the activation of sensing element 10 by examining the sensor resistance Rpvs of oxygen concentration sensing cell 15.

When sensing element 10 is not yet in the active state and hence the answer of S10 is NO, CPU 61 waits until sensing element 10 is activated. When sensing element 10 is activated, CPU 61 proceeds to a step S15 in response to the affirmative answer of S10, and starts a timer at S15, to measure time to obtain or sample values of the sensor output periodically. This operation is to start the timer whose count is stored in timer storage area 634 and updated periodically by another program performed separately. At a next step S20, the count of the timer is reset and stored in timer counter storage area 634. This resetting operation is to reset the timer to measure an elapsed time from the time of timer reset to execution of a step S45. When sensing element 10 is activated, and the answer of S10 becomes affirmative, ECU 60 further starts a drive control of sensing element 10 with sensor control circuit 31.

At a step S25 following S20, CPU 61 examines whether a predetermined engine operating condition for permitting the gas sensor diagnosis is satisfied or not. In this example, it is examined whether all of predetermined parameter conditions of engine operating parameters are satisfied continuously for a predetermined time duration. Gas sensor control device 1 monitors the engine operating parameters according to another program performed separately, and sets a confirmation flag stored in confirmation flag storage area 632 to one when all the parameter conditions of the engine operating parameters continue to valid for a time equal to or longer than the predetermined duration, and hence the engine operating condition for permitting the diagnosis is satisfied. Parameter conditions can be determined appropriately in accordance with the construction and features of the internal combustion engine. This example employs at least two parameter conditions of two engine operating parameters; the engine speed and engine temperature. The first parameter condition is met when the engine speed is higher than or equal to 2,000 rpm, and at the same time, lower than or equal to 5,000 rpm. The second parameter condition is met when the temperature of the engine cooling water is higher than or equal to 50° C., and at the same time lower than or equal to 300° C.

At S25, CPU 61 checks the confirmation flag stored in confirmation flag storage area 632 in RAM 63, and proceeds to a step S35 when the confirmation flag is zero indicating the engine operating condition for permitting the diagnosis is not satisfied, and hence the answer of S25 is NO. At step S35, CPU 61 resets five diagnostic parameters to zero, and stores the results of the resetting in parameter storage area 635 in RAM 63. As mentioned before, the five diagnostic parameters are: the local maximal value Vmax of the sensor output, the number Nm of obtained local maximal values of the sensor output, the number Nn of obtained non-maximum values of the sensor output, the number Na of over maximum values which are greater than the upper limit La, and the number Nb of obtained under maximum values which are smaller than the lower limit Lb. At a step S40 following S35, CPU 61 obtains a value of the sensor output of gas sensor 2 and stores the obtained or sampled sensor output value in sensor output storage area 633. When the confirmation flag stored in confirmation flag storage area 632 is one, indicating the fulfillment of the engine operating condition permitting the diagnosis, CPU 61 proceeds from S25 to a step S30 to perform the diagnostic process for determining whether gas sensor 2 is in the improper state incapable of functioning properly. The diagnostic process or diagnosis of S30 is shown more in detail in FIG. 6.

At a step S45 reached from S30 or S40, CPU 61 checks the timer counter storage area 634, and examines whether a predetermined time (obtaining or sampling period) has elapsed from the timer resetting operation of S20. In this example, this predetermined time is 10 msec. With step S45, CPU 61 obtains or samples instantaneous values of the gas sensor output at regular time intervals. The predetermined time (obtaining or sampling period) is not limited to 10 [msec]. The predetermine time (period) can be determined appropriately in accordance with the characteristics and/or usage of gas sensor unit 3 (or gas sensor 2). When the time (10 [msec]) is not elapsed yet, then CPU 61 waits until the expiration of the time. When the time (10 [msec]) is elapsed, CPU 61 returns from S45 to S20, and repeat the process of S20~S45 in FIG. 5.

The diagnosis of S30 is performed as shown in FIG. 6. In the diagnosis of FIG. 6, CPU 61 first looks in the measurement end flag storage area 636 and input information storage area 638 of RAM 63, and determines whether the diagnostic process is not yet performed after a turn-on of an ignition switch for the engine.

At a step S305, CPU 61 checks the measurement end flag Fe stored in measurement end flag storage area 636. When measurement end flag Fe is zero, indicating that the diagnostic process is not yet performed, and hence the answer of S305 is YES, then CPU proceeds to a step S310, and looks in the input information storage area 638 where a signal representing the condition of the fuel supply to the internal combustion engine is stored, to determine whether the fuel supply interruption (F/C) is in progress, or not. Step S310 can serve as an interruption detecting step of detecting interruption or stoppage of the supply of fuel to the engine. The interruption detecting step is not limited to the operation of S310 as long as the interruption of the fuel supply can be detected. When the fuel supply interruption is in progress, and the engine is receiving no supply of fuel, then CPU 61 proceeds from S310 to a step S315 to examine whether a predetermined time (interval) X1 is elapsed from the start of the fuel supply interruption. This predetermined time X1 is a time interval determined appropriately on the basis of a time required for changing the gas in the exhaust passage of the engine from the exhaust gases to the atmospheric air after the start of the fuel supply interruption. Predetermined time X1 is longer than the sampling period (10 [msec]) of step S45. In the example shown in FIG. 3, predetermined time X1 is 3.0 [sec] as shown by an arrow 111.

When predetermined time X1 is elapsed from the start of F/C, and hence the answer of S315 is YES, it can be assumed that the sensor output has reached a level corresponding to a level of the oxygen concentration in the atmosphere. Therefore, CPU 61 proceeds from S315 to a step S320. At step S320, CPU 61 obtains or samples a value of the sensor output from gas sensor unit 3, and stores the obtained sensor output value in sensor output storage area 633 together with the order n of sampling. The operation of S320 can serve as a sensor output obtaining or sampling step of obtaining or sampling values V(n) of the sensor output periodically at regular time intervals of a predetermined sampling or obtaining period (10 [msec]).

In the case of the negative answer of S305 because of measurement end flag Fe being one, indicating that the diagnostic process is already performed; the negative answer of S310 because of the fuel supply being not interrupted; or the negative answer of S315 because of the time X1 being not yet elapsed from the start of the fuel supply interruption: CPU 61 assumes that the condition to start the diagnosis is not yet fulfilled, and proceeds from S305, S310 or S315, to a step S450. At step S450, CPU 61 resets each of the diagnostic parameters (the local maximal value Vmax, the maximums number Nm, the non-maximums number Nn, the over maximums number Na, and the under maximums number Nb), to zero, and stores the result of the resetting in parameter storage area 635 of RAM 63. With the operation of S450 for resetting the diagnostic parameters, the diagnosis can be completed only when the condition enabling the diagnosis remains continuously. After S450, CPU 61 terminates the diagnostic process of FIG. 6 and returns to the main process of FIG. 5.

After S320, CPU 61 proceeds to a step S325, and determines a local extreme value of the sensor output. In this example, CPU 61 looks in the sensor output storage area 633; takes in a series of most recent consecutive values of the sensor output obtained consecutively; and determines a local maximal value greatest among the most recent consecutive values in the series. In this example, the number of most recent consecutive values in the series is three, the first most recent value V(n), the second most recent value V(n−1), and the third most recent value V(n−2). At step S325, CPU 61 determines whether the third most recent value V(n−2) is smaller than or equal to the second most recent value V(n−1), and at the same time the second most recent value V(n−1) is greater than the first most recent value V(n). When V(n−2) ≦V(n−1), and at the same time V(n−1)>V(n), then CPU 61 proceeds to a step S330, and regards the second most recent value V(n−1) as a local maximal value Vmax. Steps S325 and S330 can serve as an extremum determining step of determining local extreme values, such as local maximal values and/or local minimal values, of the sensor output. When the second most recent value V(n−1) (or middle value) is greater than or equal to the third most recent value V(n−2) (or preceding value), and at the same time the second most recent value V(n−1) is greater than the first most recent V(n)(or following value), then the second most recent value V(n−1) can be regarded as a local maximum forming a peak in the graph of FIG. 3.

When the number n is still 1 or 2 immediately after the end of predetermined time X1, it is possible to omit the operation of S325 since three of most recent values are not yet accumulated. It is possible to start the operation of obtaining values of the sensor output and stores values as V(n), before the end of predetermined time X1 from the start of the fuel supply interruption. For example, it is possible to obtain a value of the sensor output immediate before or immediately after step S450, and stores the obtained value in output storage area 633 together with the sampling order n. In such a case, it is possible to perform the operation of S325 with the third most recent value V(n−2) obtained before the end of X1, and the second and first most recent values V(n−1) and V(n) obtained after the end of X1. By this operation, CPU 61 can obtain a local maximum even if the value obtained first after the end of X1 is a local maximum.

When, for example, the consecutive series of three most recent values of the sensor output are values 204, 205 and 206 of the sensor signal waveform 102 shown in FIG. 4, the second most recent value 205 is stored as a local maximum (as indicated by a black circle in FIG. 4) in parameter storage area 635 at S330. When the answer of S325 is negative, on the other hand, CPU 61 proceeds from S325 to another section (S405~S430) explained later.

At a step S335 following S330, CPU 61 compares the maximum value Vmax stored at S330, with an upper limit La which is an upper limit defining a normal range of the sensor output. If a value of the sensor output is within this normal range, it is possible to judge that gas sensor 2 is in a normal or proper state. Step 335 can serve as an extremum comparing step. The upper limit La is determined from the normal range within which values of the sensor output correspond properly to the oxygen concentration of the atmosphere, and gas sensor 2 is producing values of the sensor output properly. In the example shown in FIG. 3, upper limit La is equal to 4.5 [V] as shown by a broken line 112. In the case of the sensor output value 205 stored as local maximal value Vmax, the local maximal value Vmax is greater than La (=4.5 [V]), and hence the answer of S335 is YES. Therefore, CPU 61 proceeds from S335 to a step S345, and increases the over maximums number Na by one. Thus, CPU 61 increments the over maximum number Na when a local maximal value over the normal range is obtained, and thereby counts the number of obtained over maximums which are local maximal values (Vmax) greater than La. The thus-determined over maximums number Na is stored in parameter storage area 635 at S345. Step S345 together with step S335 serves as the extremum comparing step of comparing extreme values with a predetermined threshold (such as La).

When the local maximal value Vmax is smaller than or equal to upper limit La, CPU 61 proceeds from S335 to a step S340, and compares the local maximal value Vmax stored in parameter storage area 635, with a lower limit Lb of the normal range of the gas sensor output. Step S340 can serve as at least part of the extremum comparing step. Lower limit Lb is determined from the normal range within which values of the sensor output correspond properly to the oxygen concentration of the atmosphere, and gas sensor 2 is producing values of the sensor output properly. In the example shown in FIG. 3, the lower limit Lb is equal to 3.0 [V] as shown by a broken line 113.

When the local maximal value Vmax is smaller than lower limit Lb, CPU 61 proceeds from S340 to a step S350, and increases the under maximums number Nb by one. Thus, CPU 61 increments the under maximums number Nb when a local maximal value (Vmax) under the normal range is obtained, and thereby counts the number of obtained under maximums which are local maximal values (Vmax) smaller than the lower limit Lb of the normal range. The thus-determined under maximums number Nb is stored in parameter storage area 635 at S350. Step S350 together with step S340 serves as the extremum comparing step of comparing extremum values with the predetermined threshold (such as Lb).

When the local maximal value Vmax is greater than or equal to the lower limit Lb (Vmax≧Lb), and namely the local maximal value Vmax is within the normal range, then CPU 61 proceeds from S340 directly to a step S355, detouring S350. After S345, S350 or S340 (in the case of NO), CPU 61 increments (increase by one) the maximums number Nm representing the number of obtained maximum values, and stores the maximums number Nm in parameter storage area 635, at S355 to count the number of output values regarded as local maximum.

At a step S360 following S355, CPU 61 compares the maximums number Nm stored in parameter storage area 635 with a predetermined number A to examine whether the number of obtained local maximal values becomes greater than or equal to the predetermined number A. Step S360 is to repeat the comparison of a local maximal value (Vmax) with the upper limit La until the number of repetitions reaches the predetermined number A, and to use the results of the comparisons for determining whether gas sensor 2 is in the improper condition or not. This number A corresponds to a predetermined first number. It is possible to determine the number A appropriately in accordance with the use and the characteristics of gas sensor 2 and/or the sampling period for obtaining sensor output values. In this example, number A is set equal to 15. When the maximums number Nm is smaller than A (=15), and hence the answer of S360 is NO, then CPU 61 terminates the diagnostic process of FIG. 6 and returns to the main process of FIG. 5 on the assumption that results of the comparison are not yet obtained sufficiently for the diagnosis.

When the maximums number Nm is greater than or equal to A, and hence the answer of S360 is YES, then CPU 61 proceeds to a step S365 on the assumption that results of the comparison are obtained sufficiently for the diagnosis. At S365, CPU 61 compares the over maximums number Na stored in parameter storage area 635, with a predetermined number B to determine whether or not Na is greater than or equal to B. This predetermined number B can be determined appropriately in accordance with the characteristics of gas sensor 2 and the accuracy of the diagnosis. In this example, the number B is set equal to 10. When the over maximums number Na is greater than or equal to B (=10), then CPU 61 proceeds from S365 to a step S375, and concludes that the sensitivity or gain of gas sensor 2 is too great, and the gas sensor 2 is in the improper condition (gain too great). This conclusion of the diagnosis is stored in diagnosis storage area 637 at S375.

When the over maximums number Na is smaller than B, CPU 61 proceeds from S365 to a step S370 to check the under maximums number Nb. At S370, CPU 61 compares the under maximums number Nb stored in parameter storage area 635, with a preset number which is B in this example. When the under maximums number Nb is greater than or equal to the predetermined number B, then CPU 61 proceeds from S370 to a step S380 and concludes that the sensitivity or gain of gas sensor 2 is too small, and the gas sensor 2 is in the improper condition (gain too small). This conclusion of the diagnosis is stored in diagnosis storage area 637 at S380. When the under maximums number Nb is smaller than B, CPU 61 proceeds from S370 to a step S385, and concludes that gas sensor 2 in the proper condition. This conclusion is stored in diagnosis storage area 637.

In this way, when the number Na of obtained local maximal values of the sensor output reaches predetermined number A (S360: YES), the diagnostic system according to the first embodiment checks the results (such as Na and Nb; S365 and S370) of the comparisons (S335 and S340) of the maximum values with upper and lower limits La and Lb, and determines the proper/improper condition of gas sensor 2 (S375, S380 and S385) in accordance with the results of the comparisons. Steps S365, S370, S375, S380 and S385 can serve as a diagnosing step. By using the results of comparisons accumulated to the number A, this diagnostic system can diagnose malfunction of gas sensor 2 accurately and correctly even when the sensor output is varied accidentally by an noise or some other factor. In the example shown in FIG. 6, S365 and S370 employ the same predetermined number B. However, it is optional to use different numbers between S365 and S370.

After S375, S380 or S385, CPU 61 proceeds to a step S390, at which CPU 61 sets the measurement end flag Fe to one to indicate the execution of the diagnosis, and stores the result in measurement end flag storage area 636. Step S390 is to cause the diagnostic process to be performed only once each time the ignition switch is turned on. In the next and subsequent cycles, step S305 provides a negative answer to indicate that the diagnostic process has been already performed. After S390, CPU 61 terminates the diagnostic process and returns to the main process of FIG. 5.

When the answer of step S325 is NO, CPU 61 proceeds from S325 to a step S405. When the maximum determining condition ($V(n-2) \leq V(n-1)$ and $V(n-1) > V(n)$) of S325 is not satisfied, the second most recent sensor output value $V(n-1)$ is judged to be not a local maximal value (non-maximum). For example, the sensor output value 202 shown by a white circle in FIG. 4 is smaller than the next value 203, and therefore the output value 202 is not a local maximal value. When the second most recent output value $V(n-1)$ is judged to be a non-maximum which does not satisfy the maximum determining condition of S325, then CPU 61 increments (increases by one) the number of non-maximums Nn, and stores the incremented non-maximums number Nn in parameter storage area 635 at step S405. Then, at a step S410, CPU 61 compares the non-maximums number Nn stored in parameter storage area 635, with a predetermined number C to determine whether Nn is greater than or equal to C. This operation is for performing a supplementary diagnostic operation for diagnosing malfunction of gas sensor 2 even when the sensor output does not exhibit a maximum. This number C corresponds to a predetermined second number. Number C can be determined appropriately in accordance with a sampling frequency of maximum values and the number A determining the number of maximum values. In this example, the predetermined number C is 100.

When the non-maximums number Nn is smaller than predetermined number C (=100), and the answer of S410 is NO, CPU 61 terminates the diagnostic process of FIG. 6, and returns to the main process of FIG. 5. When the non-maximums number Nn is greater than or equal to number C, CPU 61 proceeds from S410 to a step S415 to check the output value $V(n)$ stored in sensor output storage area 633. At S415, CPU 61 compares the output value $V(n)$ with the before-mentioned upper limit La and determines whether $V(n)$ is greater than La. This upper limit La corresponds to a second threshold. The upper limit used in S415 may be equal to the upper limit used in S335, or they may be unequal from each other. When the nth sensor output value $V(n)$ is greater than upper limit La, CPU 61 proceeds from S415 to a step S420, and concludes, at S420, that gas sensor 2 is in the improper condition (gain too large). The conclusion is stored in diagnosis storage area 637.

When the nth sensor output value $V(n)$ is smaller than or equal to upper limit La, CPU 61 proceeds from S415 to a step S425, concludes that gas sensor 2 is in the proper condition, and stores the conclusion in diagnosis storage area 637 at S425. Thus, when the non-maximums number Nn reaches predetermined number C (S410: YES), the diagnostic system compares the nth (or most recent) sensor output value $V(n)$ at the time of attainment of C by the non-maximums number Nn, with the second threshold level (upper limit La)(S415), and determines whether gas sensor 2 is in the improper condition or not (S420, S425) in accordance with the result of the comparison. Steps S410, S415, S420 and S425 correspond to the diagnosing step.

After S420 or S425, CPU 61 proceeds to a step S430, sets the measurement end flag Fe to one, and stores the updated value of measurement end flag Fe in measurement end flag storage area 636, at S430 in the same manner as step S390. Then, CPU 61 terminates the diagnostic process of FIG. 6, and returns to the main process of FIG. 5.

The diagnostic system according to the first embodiment performs the diagnostic process in this way. The diagnostic system may be arranged to notify the user, of the result of the diagnosis by audible or visible message with the output device 91 including a device such as a display, a warning device or lamp, or a speaker, or may be arranged to supply the result of the diagnosis to external equipment through an output terminal for the diagnosis, or by serial communication.

In the first embodiment, step S310 corresponds to an element for detecting an interruption of fuel supply to an internal combustion engine, by looking in the input information storage area 638 in this example, and CPU 61 serves as means for detecting the interruption of fuel supply to the engine. Step S320 corresponds to an element for obtaining one or more sensor output values of the gas sensor output at regular time intervals of a predetermined obtaining period, and CPU 61 serves as means for obtaining sensor output values at regular time intervals. Steps S325 and S330 correspond to an element for determining local extreme values (such as local maximum or local minimum) each of which is an extremum in a series of sensor output values obtained consecutively after the elapse of a predetermined time X1, and CPU 61 serves as means for determining local extreme values.

At least one of steps S335, S345, S340 and S350 can correspond to an element for comparing the local extreme values with a first predetermined threshold level (such as La and Lb), and CPU 61 can serve as means for comparing the local extreme values with the first threshold level. In the case of FIG. 6, as the means for comparing the local extreme values with the first threshold value, CPU 61 compares the local maximum values Vmax determined at S330, with upper limit La as the first predetermined threshold level at S335 and counts the over maximums number Na (S345). Similarly, as the means for comparing the local extreme values with the first threshold value, CPU 61 compares the local maximum values Vmax with lower limit Lb as the first predetermined threshold level at S340 and counts the under maximums number Nb (S350). At least one of S365, S370, S375, S380 and S385 can correspond to an element for determining whether the gas sensor 2 is in the improper condition or not, in accordance with results of the comparison of local extreme values with the first threshold level, and CPU 61 can serve as means for diagnosing the improper condition of gas sensor 2. In the case of FIG. 6, when a predetermined number of local maximal values are obtained (S360: YES), CPU 61 (serving as the means for diagnosing the improper condition of gas sensor 2) determines whether gas sensor 2 is in the improper condition or not (S375, S380, S385), by using the results of comparisons (S335, S340) of the obtained local maximal values (S365, S370). Moreover, when the non-maximums number Nn reaches predetermined number C (S410: YES), CPU 61 of this example further serves as the diagnosing means by comparing the sensor output value at the time of attainment of predetermined C (S410: YES), with the upper limit La as the second threshold level (S415), and thereby determining whether gas sensor 2 is in the improper condition or not (S420, S425).

The diagnostic system according to the first embodiment is arranged to compare a plurality of local extreme values of the sensor output with the first threshold level, and to determine the improper/proper condition of gas sensor 2 in accordance with the results of comparisons of the local extreme values. Therefore, the diagnostic system can determine the condition of gas sensor 2 accurately without being influenced by incidental fluctuation of the sensor output. Moreover, the diagnostic system of the first embodiment is arranged to determine the condition of gas sensor 2 when the number of obtained extreme values reaches first predetermined number A or when the number of non-extreme values reaches second predetermined number C. Therefore, the diagnostic system can perform the diagnosis promptly before cancellation of the fuel supply interruption.

The diagnostic system of the first embodiment is arranged to obtain sensor output values after the elapse of the predetermined time X1 determined in accordance with the time required for replacement of exhaust gas around gas sensor 2 by fresh air, and determine extreme values by using the sensor output values obtained after the elapse of the predetermined time X1. Therefore, the diagnostic system can determine extreme values in the state in which the waveform of the sensor output has become stable, and thereby perform the diagnosis accurately. The diagnostic method and apparatus can detect the improper condition of gas sensor 2 accurately, and encourage replacement of gas sensor 2 to prevent an increase of harmful component in the exhaust gases.

Figure 7:
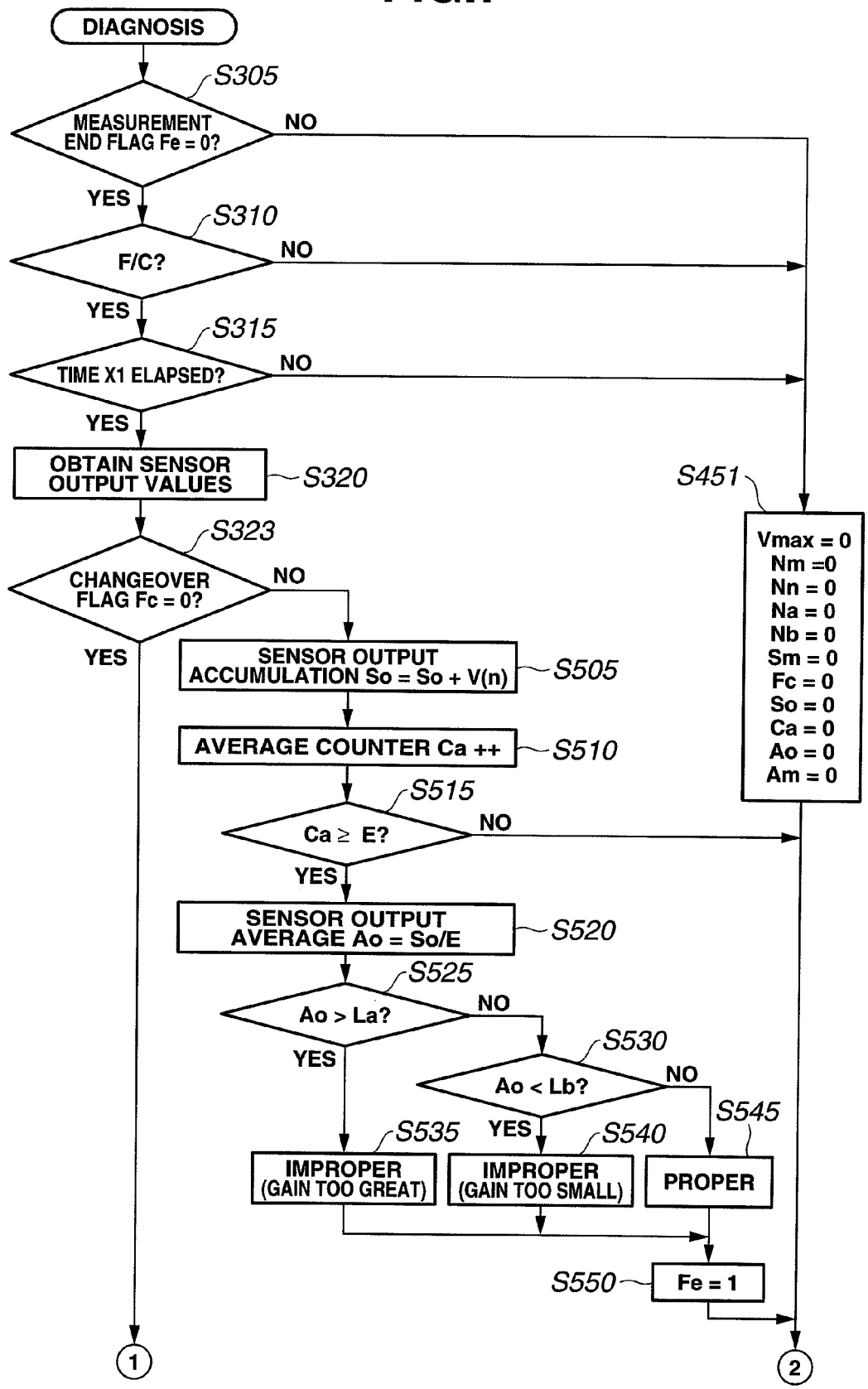
FIG. 7 is a flowchart showing a first part of a diagnostic process performed in the main process of FIG. 5, according to a second embodiment of the present invention.
Figure 8:
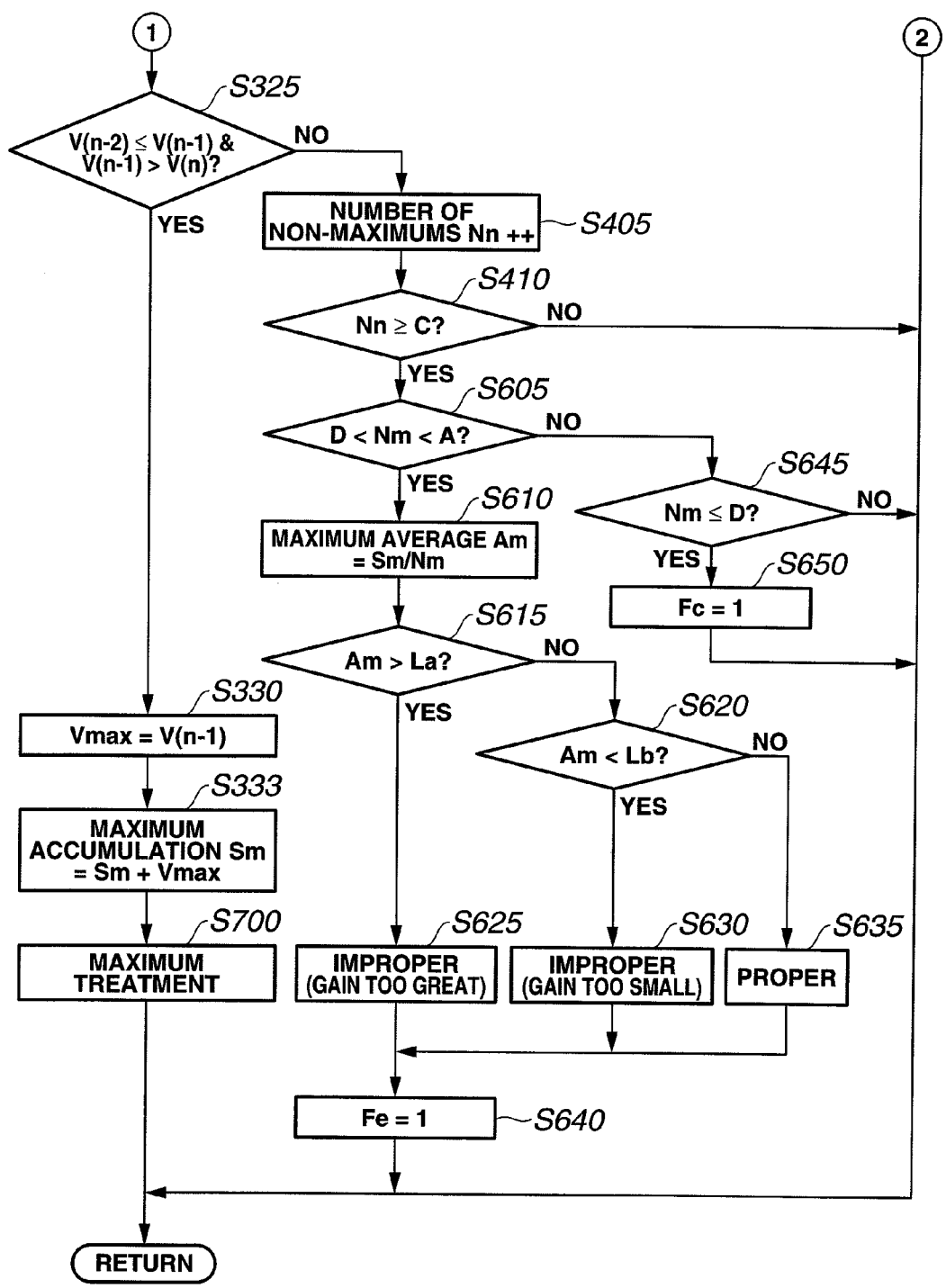
FIG. 8 is a flowchart showing a second part of the diagnostic process performed in the main process of FIG. 5, according to the second embodiment.

FIGS. 7 and 8 show a diagnostic method according to a second embodiment of the present invention. The diagnostic method of the second embodiment is different from that of the first embodiment in the process after the non-maximums number Nn reaches predetermined number C.

The gas sensor system according to the second embodiment is substantially identical in structure to the system shown in FIG. 1, so that repetitive explanation is omitted. Specifically, the gas sensor control device 1 of the second embodiment is substantially identical in physical structure to the gas sensor control device 1 of the first embodiment. RAM 63 according to the second embodiment has a structure of storage areas slightly different from that of the first embodiment. In addition to the storages areas 631~638 shown in FIG. 2, RAM 63 of the second embodiment has a diagnostic mode changeover flag storage area for storing a diagnosis changeover flag Fc to change over the mode of diagnosis used when the non-maximums number Nn becomes greater than or equal to C. Moreover, the parameter storage area 635 in RAM 63 stores additional or secondary diagnostic parameters used for the diagnosis performed complementarily when $Nn \geq C$, in addition to the diagnostic parameters employed in the first embodiment. The secondary diagnostic parameters used additionally in the second embodiment are: a maximum accumulation Sm for accumulating local maximal values; a maximum average Am (=Sm/Nm) obtained by dividing the maximum accumulation Sm by the maximums number Nm; and a sensor output accumulation So for accumulating sensor output values when diagnosis changeover flag Fc is one. Parameter storage area 635 in RAM 63 according to the second embodiment further stores an average (or averaging) counter Ca for counting the number of sensor output values accumulated in the sensor output accumulation So, and a sensor output average Ao (=So/Ca) obtained by dividing the sensor output accumulation So by the average counter Ca.

A main process according to the second embodiment is almost the same as the main process shown in FIG. 5. The main process of the second embodiment is different from that of the first embodiment only in steps S5, S30 and S35. At S5 and S35 according to the second embodiment, the additional or secondary diagnostic parameters are initialized as well as the diagnostic parameters which are used in the first embodiment and which can be referred to as primary diagnostic parameters merely to distinguish them from the secondary diagnostic parameters. At S5 and S35, CPU 61 of the second embodiment resets the diagnostic parameters to zero, and stores the results of the resetting in parameter storage area 635 in RAM 63. In addition to the local maximal value Vmax of the sensor output, the number Nm of obtained local maximal values of the sensor output, the number Nn of obtained non-maximum values of the sensor output, the number Na of over maximum values greater than upper limit La, and the number Nb of obtained under maximum values smaller than the lower limit Lb, CPU 61 resets each of the maximum accumulation Sm, diagnosis changeover flag Fc, sensor output accumulation So, average counter Ca, sensor output average Ao and maximum average Am, to zero, and stores the results in the diagnosis changeover flag storage area or the parameter storage area 635.

The diagnosis of S30 is arranged as shown in FIGS. 7 and 8 in the case of the second embodiment. In this example, CPU 61 shown in FIG. 1 performs the process of FIGS. 7 and 8 according a program stored in ROM 62, as well as other programs performed by ECU 60. The diagnostic process shown in FIGS. 8 and 9 includes steps substantially identical to steps shown in FIG. 6. Therefore, these steps are given the same step numbers and their detailed explanation is omitted or simplified.

Steps S305, S310 and S315 in FIG. 7 are substantially identical to S305, S310 and S315 of FIG. 6. When at least one of the conditions of S305, S310 and S315 is not satisfied, CPU 61 proceeds from S305, S310 or S315, to a step S451. At S451, CPU 61 resets the primary diagnostic parameters Vmax, Nm, Nn, Na and Nb to zero, and stores the results in parameter storage area 635 of RAM 63 like step S450 of FIG. 6. At S451, moreover, CPU 61 further resets the secondary diagnostic parameters including the maximum accumulation Sm, sensor output accumulation So, sensor output average Ao, maximum average Am, the diagnosis changeover flag Fc and average counter Ca to zero, and stores the results in the parameter storage area 635 or the changeover flag storage area. After S451, CPU 61 terminates the diagnostic process of FIGS. 7 and 8 and returns to the main program of FIG. 5.

After the end of predetermined time X1 from a start of interruption of the fuel supply to the engine, CPU 61 proceeds from S315 to step S320, and obtains a sensor output value in the same manner as in S320 of FIG. 6. After S320, CPU 61 checks, at a step S323, the diagnosis changeover flag Fc stored in the changeover flag storage area in RAM 63. When changeover flag Fc is not equal to zero, CPU 61 proceeds to a section of steps S505~S550 as explained later. When changeover flag Fc is zero, CPU 61 proceeds from S323 to step S325 shown in FIG. 8, and checks the maximum determining condition (V(n−1)≧V(n−2) & V(n−1)>V(n)) in the same manner as step S325 shown in FIG. 6.

When the (n−2)th sensor output value V(n−2) is smaller than or equal to the (n−1)th sensor output value V(n−1), and at the same time the (n−1)th sensor output value V(n−1) is greater than the nth sensor output value V(n), then CPU 61 performs the operation of step S330 as in the first embodiment. After S330, CPU 61 proceeds to a step S333. At S333, CPU 61 adds the maximum value Vmax determined at S330, to the maximum accumulation Sm (Sm=Sm+Vmax), and stores the result in parameter storage area 635. Thereafter, CPU 61 proceeds to a step S700 for maximum treatment, and performs the operations of S335~S390 shown in FIG. 6, at S700.

When the second most recent value V(n−1) does not satisfy the maximum determining condition (V(n−1)≧V(n−2) & V(n−1)>V(n)) of S325, and hence the answer of S325 is NO, then CPU 61 performs the operations of steps S405 and S410 as in the first embodiment. When the non-maximums number Nn is smaller than predetermined number C, and the answer of S410 is NO, then CPU 61 terminates the diagnostic process of FIGS. 7 and 8, and returns to the main program of FIG. 5. When the non-maximums number Nn is greater than or equal to predetermined number C, and the answer of S410 is YES, then CPU 61 proceeds to a step S605 to examine whether the maximums number Nm is within a predetermined range. At S605 of this example, CPU 61 checks the maximums number Nm stored in parameter storage area 635, and examines whether the maximums number Nm is greater than a predetermined number D and at the same time smaller than a predetermined number A (which is greater than D). The operation of S605 is an operation to select one of different diagnostic modes in accordance with the number Nm of maximum values at the time when the non-maximums number Nn reaches C. Predetermined numbers A and D can be determined in accordance with the usage and characteristics of gas sensor 2, and the obtaining (or sampling) period of obtaining (or sampling) values of the gas sensor output. In this example, the predetermined number A is set equal to 15 as in the example (S360) of FIG. 6, and the predetermined number D is set equal to 5.

When the maximums number Nm is smaller than or equal to D (=5), or the maximums number Nm is greater than or equal to A (=15), and the answer of S605 is NO, then CPU 61 proceeds from S605 to a step S645, and compares the maximums number Nm with a predetermined number D to determine whether Nm is smaller than or equal to D. When the maximums number Nm is smaller than or equal to D (Nm≦D), and the answer of S645 is YES, then CPU 61 proceeds to a step S650, sets the diagnosis changeover flag Fc to one, and stores the result in the diagnosis changeover flag storage area of RAM 63. When the diagnosis changeover flag Fc is one, the diagnostic system enters the secondary diagnostic section of S505~S550 based on the sensor output average Ao after the non-maximums number Nn reaches C. After S650, CPU 61 terminates the diagnostic process and returns to the main process of FIG. 5. When the maximums number Nm is greater than D, and the answer of S645 is NO, then CPU 61 terminates the diagnostic process and returns to the main process of FIG. 5, detouring S650.

When the maximums numbers Nm is greater than predetermined number D and smaller than predetermined number A, and the answer of S605 is YES, then CPU 61 proceeds to a step S610, and calculates the maximum average Am by dividing the maximum accumulation Sm by the maximums number Nm (Am=Sm/Nm). The thus-calculated maximum average Am is stored in parameter storage area 635. The thus-determined maximum average Am corresponds to an value obtained by averaging extreme values of the sensor output. Then, at a step S615, CPU 61 compares the maximum average Am stored in parameter storage area 635, with upper limit La, and determines whether maximum average Am is greater than La. The upper limit La used in S615 corresponds to a fourth threshold. When the maximum average Am is greater than upper limit La, then CPU 61 proceeds from S615 to a step S625, and concludes that the sensitivity or gain of gas sensor 2 is too great, and the gas sensor 2 is in the improper condition (gain too great). This conclusion of the diagnosis is stored in diagnosis storage area 637 at S625.

When the maximum average Am is smaller than or equal to La, CPU 61 proceeds from S615 to a step S620 to compare the maximum average Am with lower limit Lb. The lower limit Lb used in S620 can correspond to the fourth threshold, together with upper limit La. When the maximum average Am is smaller than lower limit Lb, then CPU 61 proceeds from S620 to a step S630, and concludes that the sensitivity or gain of gas sensor 2 is too small, and the gas sensor 2 is in the improper condition (gain too small). This conclusion of the diagnosis is stored in diagnosis storage area 637 at S630. When maximum average Am is greater than or equal to lower limit Lb, and the answer of S620 is NO, then CPU 61 proceeds from S620 to a step S635, and concludes, at S635, that gas sensor 2 is in the proper condition. The conclusion is stored in the diagnosis storage area 637, at S635.

In this way, when the non-maximums number Nn reaches the predetermined number C, the diagnostic system examines whether gas sensor 2 is in the proper condition or not, in accordance with the maximum average Am. In the illustrated example, the maximum average Am is compared with the fourth threshold including La and/or Lb. Steps S615, S620, S625, S630 and S635 can correspond to the diagnosing step. In the illustrated example, the fourth threshold includes upper limit La and lower limit Lb and the upper and lower limits La and Lb are equal to La and Lb used in S335 and S340 of FIG. 6. However, it is optional to employ the fourth threshold different from La and Lb used in S335 and S340 of FIG. 6. It is possible to employ, as the fourth threshold, either one of La and Lb though the use of both La and Lb is preferable in view of the accuracy of the diagnosis.

After S625, S630 or S635, CPU 61 proceeds to a step S640, and sets the measurement end flag Fe to one to indicate that the diagnosis is finished, and stores the result in measurement end flag storage area 636, at S640. The operation of S640 is substantially identical to S390 of the first embodiment. After S640, CPU 61 terminates the diagnostic process of FIGS. 7 and 8, and returns to the main program of FIG. 5.

When the changeover flag Fc is one, and the answer of S323 is NO, then CPU 61 proceeds from S323 to a step S505. At S505, CPU 61 adds the sensor output value obtained at S320, to the sensor output accumulation So (So=So+V(n)), and stores the result in parameter storage area 653. At a next step S510, CPU 61 increments (increases by one) the average (or averaging) counter Ca, and stores the result in parameter storage area 635. Then, at a step S515, CPU 61 checks the average counter Ca stored in parameter storage area 635, and compares the average counter Ca with a predetermined number E to determine whether Ca is greater than or equal to E. This number E corresponds to a third predetermined number. Number E is determined appropriately in accordance with the use and characteristics of gas sensor 2 and the obtaining period for obtaining sensor output values. In this example, number E is set equal to five. When average counter Ca is smaller than E (=5), and the answer of S515 is NO, CPU 61 terminates the diagnostic process, and returns to the main process of FIG. 5. When average counter Ca is greater than or equal to E, and the answer of S515 is YES, CPU 61 proceeds from S515 to a step S520 to calculate the sensor output average Ao. At S520, CPU 61 calculates the sensor output average Ao by dividing the sensor output accumulation So by E (or average counter Ca), and stores the thus-calculated sensor output average Ao in parameter storage area 635. This sensor output average Ao corresponds to a value obtained by averaging sensor output values which are equal to E in number.

Then, at steps S525 and S530, CPU 61 checks the sensor output average Ao stored in parameter storage area 635. At S525, CPU 61 compares sensor output average Ao with upper limit La, and determines whether Ao is greater than or not. Upper limit La used in S525 corresponds to the second threshold, and the third threshold. When sensor output average Ao is greater than upper limit La, and the answer of S525 is YES, CPU 61 proceeds to a step S535, and concludes that the sensitivity or gain of gas sensor 2 is too great, and the gas sensor 2 is in the improper condition (gain too great). This conclusion of the diagnosis is stored in diagnosis storage area 637 at S535.

When the sensor output average Ao is smaller than or equal to La, CPU 61 proceeds from S525 to step S530 to compare the sensor output average Ao with lower limit Lb. The lower limit Lb used in S530 can correspond to the second threshold and third threshold, together with upper limit La. When the sensor output average Ao is smaller than lower limit Lb, then CPU 61 proceeds from S530 to a step S540, and concludes that the sensitivity or gain of gas sensor 2 is too small, and the gas sensor 2 is in the improper condition (gain too small). This conclusion of the diagnosis is stored in diagnosis storage area 637 at S540. When sensor output average Ao is greater than or equal to lower limit Lb, and the answer of S530 is NO, then CPU 61 proceeds from S530 to a step S545, and concludes, at S545, that gas sensor 2 is in the proper condition. The conclusion is stored in diagnosis storage area 637, at S545.

Thus, when the non-maximums number Nn becomes equal to predetermined number C (S410: YES), the diagnostic system of the second embodiment accumulates sensor output values obtained after the non-maximums number Nn becomes equal to C until the number of thus-accumulated sensor output values becomes equal to E, and examines the thus-accumulated sensor output values to determine whether gas sensor 2 is in the improper condition or not. More specifically, the diagnostic system calculates the sensor output average Ao by averaging the accumulated sensor output values obtained after the non-maximums number Nn reaches C, and compares the thus-calculated sensor output average Ao with upper and lower limits La and Lb (S525, S530) to determine whether gas sensor 2 is in the improper condition or not. Steps S525, S530, S535, S540 and S545 correspond to the diagnosing step. In the illustrated example, the third threshold (or second threshold) includes upper limit La and lower limit Lb and the upper and lower limits La and Lb are equal to La and Lb used in S335 and S340 of FIG. 6. However, it is optional to employ one or more threshold values different from La and Lb used in S335 and S340 of FIG. 6. It is possible to employ, as the third threshold (or second threshold), either one of La and Lb though the use of both La and Lb is preferable in view of the accuracy of the diagnosis.

At a step S550 after S535, S540 or S545, CPU 61 sets the measurement end flag Fe to one to indicate the execution of the diagnostic process, and stores the measurement end flag Fe in measurement end flag storage area 636. This operation is substantially identical to the operation of S390 or S430 of FIG. 6. After S550, CPU 61 terminates the diagnostic process and returns to the main process of FIG. 5.

When the non-maximums number Nn reaches the predetermined number C (S410: YES), CPU 61 serving as diagnosing means determines the proper/improper condition of gas sensor 2, by checking the sensor output average Ao determined by averaging a predetermined number (E) of sensor output values obtained after the non-maximums number Nn reaches the predetermined second number (C) which may be greater than the first predetermined number (A), or by checking the maximum average Am.

When the non-maximums number Nn becomes equal to the second predetermined number (C)(S410: YES), CPU 61 of the second embodiment changes over the diagnosis between a first mode (S525, S530) based on the sensor output average Ao and a second mode (S615, S620) based on the maximum average Am, in accordance with the maximums number Nm. When the maximums number Nm is smaller than or equal to predetermined number D(5)(S645: YES), the first mode is selected (by setting changeover flag Fc to one at S650). When the maximums number Nm is greater than predetermined number D(5) and smaller than predetermined number A(15)(S605: YES), the second mode is selected.

In the first mode (S505, S510, S515, S520, S525, S530, S535, S540, S545 and S550), the diagnostic system determines the sensor output average Ao by averaging a predetermined number (E) of sensor output values obtained after the non-maximums number Nn becomes equal to number C (S520), and determines the proper/improper condition of gas sensor 2 by comparing the sensor output average Ao with the third threshold level (La, Lb). By using the sensor output average Ao for diagnosis, the diagnostic system can reduce undesired influence by a sensor output value produced by noise or other accidental factor, as compared to the diagnosis using only one sensor output value.

In the second mode (S610, S615, S620, S625, S630, S635 and S640), the diagnostic system calculates the average Am of maximum value obtained so far, and determines the proper/improper condition of gas sensor 2 by comparing the maximum average Am with the fourth threshold level (La, Lb).

Thus, the diagnostic system of the second embodiment can determine the proper/improper condition of the gas sensor accurately in a supplementary manner even when the diagnostic system is unable to collect a sufficient number of extreme values of the gas sensor output because of influence of engine operating conditions before the detection of the interruption of the fuel supply. Moreover, the diagnostic system according to the second embodiment changes over the diagnosis in accordance with the maximums number Nm, and thereby determines the proper/improper condition of the gas sensor accurately by the diagnostic mode suitable to the maximums number Nm.

The present invention is not limited to the concrete examples of the first and second embodiments. Various modifications and variations are possible within the purview of the present invention. For example, the gas sensor for sensing a condition of a specified gas component is not limited to the oxygen sensor employed in the first and second embodiments. The specified gas component may be HC, CO or NOx, the gas sensor may be a sensor for sensing one or more of these gas components, and the diagnosis may be performed for determining the proper/improper condition of such a gas sensor.

It is possible to omit either one of the over-gain detecting diagnostic operation (such as S365 and S415) for detecting abnormality of excessively high gain of the gas sensor, and the under-gain detecting diagnostic operation (such as S370) for detecting abnormality of excessively low gain. However, it is preferable to perform both of the over gain detecting diagnostic operation and the under-gain detecting diagnostic operation by using the upper limit and lower limit, in order to improve the accuracy of the diagnosis.

The extremum determining operation is not limited to the operation of S325 using the first most recent sensor output value V(n), second most recent sensor output value V(n−1) and third most recent sensor output value V(n−2). It is possible to use four or more recent sensor output values for determining an extreme value. If the recurring period of extreme values is known before or predictable, the diagnostic system or method may be arranged to determine a first extreme value after the start of the extremum determining step by using three consecutive sensor output values, and thereafter to determine an extreme value in accordance with the timing of determination of the first extreme value and the recurring frequency of extreme values.

It is possible to use, as the extreme values for diagnosis, local minimal values instead of local maximal values, or to use both of local minimal values and local maximal values. In the illustrated examples, the gas sensor diagnostic process is performed only once each time the ignition switch is turned on. However, the invention is not limited to this. The diagnostic system or method may be arranged to perform the diagnostic process two or more times during the on period of the ignition switch from a turn-on to a turn-off.

In the illustrated examples, the diagnostic system uses the over maximums number Na of maximum values greater than upper limit La, and compares the over maximums number Na with predetermined number B (S365) to detect the over-gain abnormality (S375). However, the present invention is not limited to this. For example, the diagnostic system may be arranged to determine extreme values smaller than an upper limit at S335, to count the number of extreme values smaller than the upper limit, to examine whether the number of extreme values smaller than the upper limit is smaller than predetermined number B at S365, and to conclude that the gas sensor in the improper condition with the sensor gain being too great when the number of extreme values smaller than the upper limit is smaller than predetermined number B. Similar variations are possible for the steps S340 and S370, and for the step S700 of the second embodiment.

At S415, the most recent sensor output value V(n) is compared with upper limit La to determine whether the gas sensor in the improper condition or not. Similarly, the diagnostic system may be arranged to compare the most recent sensor output value V(n) with lower limit Lb, to conclude that the gas sensor is in the improper condition with the sensor gain being too small when the most recent sensor output value V(n) is smaller than lower limit Lb, and to conclude that the gas sensor is in the proper condition when the most recent sensor output value V(n) is greater than or equal to lower limit Lb. Furthermore, the diagnostic system may be arranged to check two or more sensor output values obtained after Nn becomes equal to C, to compare each sensor output value with upper limit La at S415, and to determine whether the gas sensor is in the improper condition or not, in accordance with the results of comparison with upper limit La at S415.

When the non-maximums number Nn reaches predetermined number C (S410: YES), the diagnostic process of FIGS. 7 and 8 changes over the diagnosis between the first mode (S520~S550) and the second mode (S610~S640), in accordance with the maximums number Nm. However, the present invention is not limited to this. For example, the diagnostic method may be arranged to perform either of the first mode (S520~S550) and the second mode (S610~S640) without regard to the maximums number Nm. Moreover, the diagnostic method may be arranged to change over the diagnosis between one of the first mode (S520~S550) and the second mode (S610~S640) of the second embodiment, and a mode (S415, S420, S425, S430) according to the first embodiment, in accordance with the maximums number Nm. The second mode (S610~S640) is not feasible unless one or more extreme values are obtained when the number C is reached (S410: YES). Therefore, it is preferable to employ another diagnostic mode, such as the first mode (S520~S550), which is feasible even when the second mode (S610~S640) is unfeasible.

Various variations of the diagnostic mode of S520~S550 are possible. This section (S520~S550) of the diagnostic method according to the second embodiment is arranged to determine whether the gas sensor is in the improper condition or not, by comparing a (third) diagnostic parameter with a (third) threshold level. The (third) diagnostic parameter may be sensor output accumulation So of sensor output values obtained after predetermined number C is reached (S410: YES). In this case, the diagnostic system determines whether the gas sensor in the improper condition or not by comparing the sensor output accumulation So with the (third) threshold level.

The third threshold (second threshold) and the fourth threshold of the second embodiment are set at values used for the first threshold in the first embodiment. However, the present invention is not limited to this. It is possible to set different values for these thresholds.

According to the first and second embodiments of the present invention, a gas sensor diagnostic method or apparatus comprises (1) a sensor output obtaining element (such as a step or a section) for obtaining sensor output values of the gas sensor output at regular time intervals of a predetermined obtaining period; (2) an interruption detecting element for detecting a fuel supply interruption to the engine; (3) an extremum determining element of determining local extreme values during a period of fuel supply interruption; (4) an extremum comparing element for comparing the local extreme values with a first predetermined threshold level; and (5) a diagnosing element for determining whether the gas sensor is in the improper condition or not, by using results of the comparison of the local extreme values with the first threshold level when an extrema number becomes equal to a predetermined first number (A), the extrema number being the number (Nm) of the local extreme values obtained from the gas sensor output.

Moreover, according to the first and second embodiments, the diagnostic method or apparatus may further comprise a discriminating element (step or section) for counting the before-mentioned extrema number and a number (or non-extrema number) (Nn) of non-extreme values each of which is a sensor output value and which is not judged to be an extreme value (or which does not satisfy an extreme determining condition such as the maximum determining condition of S325), and for selecting one of primary and secondary diagnostic modes in accordance with the extrema number (Nm) and the non-extrema number (Nn). The discriminating element may be a subelement of the extremum determining element. In the first and second embodiments, the discriminating element selects the primary diagnostic mode when the extrema number (Nm) is greater than or equal to the first predetermined number (A), and selects the secondary diagnostic mode when the non-extrema number (Nn) is greater than or equal to a second predetermined number (C) which may be greater than the first predetermined number (A). The diagnosing element may be arranged to determine the improper/proper condition of the gas sensor by using a first diagnostic parameter determined from the results of the comparison of the local extreme values with the first threshold level in the primary diagnostic mode; and by using a second diagnostic parameter for comparison with a second threshold level in the second diagnostic mode. The first diagnostic parameter used in the primary diagnostic mode may include the number of extreme values greater than or smaller than the first threshold level, such as the before-mentioned over-maximums number Na or under-maximums number Nb. The second diagnostic parameter used in the secondary diagnostic mode may be determined from a sensor output value (V(n)) obtained after the non-extrema number (Nn) reaches the second predetermined number (C).

The secondary diagnostic mode may include first and second modes as in the second embodiment. In this case, the discriminating element may be configured to select one of the first and second modes in accordance with the extrema number. In the first mode, the diagnosing element may use a mean that typifies a set of sensor output values, as the second diagnostic parameter. For example, the mean may be an arithmetic mean or may be a weighted mean or average of sensor output values. In the illustrated example of the second embodiment, the diagnosing element uses the sensor output average Ao as the second diagnostic parameter, and compares the sensor output average Ao with the third threshold level. In the second mode, the diagnostic element may use a mean typifying a sent of extreme values of the sensor output. For example, the means may be an arithmetic mean or may be a weighted mean or average of local extreme (maximal or minimal) values of the sensor output. In the illustrated example of the second embodiment, the diagnosing means uses the average Am of maximum values, and compares the maximum average Am with the fourth threshold level.

This application is based on two prior Japanese Patent Applications No. 2007-040940 filed on Feb. 21, 2007, and No. 2007-166612 filed on Jun. 25, 2007. The entire contents of these Japanese Patent Applications No. 2007-040940 and No. 2007-166612 are hereby incorporated by reference.

Although the invention has been described above by reference to certain embodiments of the invention, the invention is not limited to the embodiments described above. Modifications and variations of the embodiments described above will occur to those skilled in the art in light of the above teachings. The scope of the invention is defined with reference to the following claims.

What is claimed is:

1. A gas sensor diagnostic method of diagnosing an improper condition of a gas sensor for producing a gas sensor output representing a concentration of a specified gas component in an exhaust gas mixture of an internal combustion engine, comprising:
   a sensor output obtaining step of obtaining sensor output values of the gas sensor output at regular time intervals of a predetermined obtaining period;
   an interruption detecting step of detecting a fuel supply interruption to the engine;
   an extremum determining step of determining local extreme values each of which is an extremum in a series of sensor output values obtained consecutively by the sensor output obtaining step during a fuel supply interruption period during which the fuel supply interruption is detected by the interruption detecting step;
   an extremum comparing step of comparing each of the local extreme values with a first predetermined threshold level; and
   a diagnosing step of determining whether the gas sensor is in the improper condition or not, in accordance with results of the comparison of the local extreme values with the first threshold level when a number of the local extreme values obtained from the gas sensor output becomes equal to a predetermined first number.

2. The gas sensor diagnostic method as claimed in claim 1, wherein the local extreme values are determined from sensor output values obtained after the lapse of a predetermined time interval which is longer than the obtaining period, from detection of the fuel supply interruption.

3. The gas sensor diagnostic method as claimed in claim 1, wherein the extremum determining step includes an operation of checking a series of first, second and third sensor output values obtained consecutively by the sensor output obtaining step, and examining the second sensor output value obtained after the first sensor output value and before the third sensor output value, to determine whether the second output value is a local extreme value or not.

4. The gas sensor diagnostic method as claimed in claim 1, wherein the extremum comparing step includes an operation of counting a number of over extreme values each of which is a local extreme value greater than an upper limit set as the first threshold level, and the diagnosing step includes an operation of determining whether the gas sensor is in the improper condition or not, in accordance with the number of the over extreme values.

5. The gas sensor diagnostic method as claimed in claim 1, wherein the extremum comparing step includes an operation of counting a number of under extreme values each of which is a local extreme value smaller than a lower limit set as the first threshold level, and the diagnosing step includes an operation of determining whether the gas sensor is in the improper condition or not, in accordance with the number of the under extreme values.

6. The gas sensor diagnostic method as claimed in claim 1, wherein the diagnosing step includes an operation of determining whether the gas sensor is in the improper condition or not, by comparing, with a second threshold level, at least one sensor output value of the gas sensor output obtained after a number of non-extreme values reaches a second predetermined number, each of the non-extreme values being a sensor output value which is not judged to be a local extreme value.

7. The gas sensor diagnostic method as claimed in claim 1, wherein the diagnosing step includes an operation of determining whether the gas sensor is in the improper condition or not, by comparing, with a third threshold level, an average of sensor output values of the gas sensor output obtained after a number of non-extreme values reaches a second predetermined number, each of the non-extreme values being a sensor output value which is not judged to be a local extreme value.

8. The gas sensor diagnostic method as claimed in claim 1, wherein the diagnosing step includes an operation of determining whether the gas sensor is in the improper condition or not, by comparing, with a fourth threshold level, an average of extreme values when a number of non-extreme values reaches a second predetermined number, each of the non-extreme values being a sensor output value which is not judged to be a local extreme value.

9. A gas sensor control apparatus to diagnose an improper condition of a gas sensor for producing a gas sensor output representing a concentration of a specified gas component in an exhaust gas mixture of an internal combustion engine, comprising:
a sensor output obtaining section to obtain sensor output values of the gas sensor output at regular time intervals of a predetermined obtaining period;
an interruption detecting section to detect a fuel supply interruption to the engine;
an extremum determining section to determine local extreme values each of which is an extremum in a series of sensor output values obtained consecutively by the sensor output obtaining section during a fuel supply interruption period during which the fuel supply interruption is detected by the interruption detecting section;
an extremum comparing section to compare each of the local extreme values with a first predetermined threshold level; and
a diagnosing section to determine whether the gas sensor is in the improper condition or not, in accordance with results of the comparison of the local extreme values with the first threshold level when a number of the local extreme values obtained from the gas sensor output becomes equal to a predetermined first number.

10. The gas sensor control apparatus as claimed in claim 9, wherein the extremum determining section is configured to determine the local extreme values from sensor output values obtained after the lapse of a predetermined time interval which is longer than the obtaining period, from detection of the fuel supply interruption by the interruption detecting section.

11. The gas sensor control apparatus as claimed in claim 9, wherein the extremum determining section is configured to check a series of first, second and third sensor output values obtained consecutively by the sensor output obtaining section, and to examine the second sensor output value obtained after the first sensor output value and before the third sensor output value, to determine whether the second output value is a local extreme value or not.

12. The gas sensor control apparatus as claimed in claim 9, wherein the extremum comparing section is configured to count a number of over extreme values each of which is a local extreme value greater than an upper limit set as the first threshold level, and the diagnosing section is configured to determine whether the gas sensor is in the improper condition or not, in accordance with the number of the over extreme values.

13. The gas sensor control apparatus as claimed in claim 9, wherein the extremum comparing section is configured to count a number of under extreme values each of which is a local extremum value smaller than a lower limit set as the first threshold level, and the diagnosing section is configured to determine whether the gas sensor is in the improper condition or not, in accordance with the number of the under extreme values.

14. The gas sensor control apparatus as claimed in claim 9, wherein the extremum determining section is configured to count a number of non-extreme values each of which is a sensor output value which is not judged to be a local extreme value; and the diagnosing section is configured to determine whether the gas sensor is in the improper condition or not, by comparing, with a second threshold level, at least one sensor output value of the gas sensor output obtained after the number of non-extreme values reaches a second predetermined number.

15. The gas sensor diagnostic apparatus as claimed in claim 9, wherein the extremum determining section is configured to count a number of non-extreme values each of which is a sensor output value which is not judged to be a local extreme value; and the diagnosing section is configured to determine whether the gas sensor is in the improper condition or not, by comparing, with a third threshold level, an average of sensor output values of the gas sensor output obtained after the number of non-extreme values reaches a second predetermined number.

16. The gas sensor diagnostic apparatus as claimed in claim 9, wherein the extremum determining section is configured to count a number of non-extreme values each of which is a sensor output value which is not judged to be a local extreme value; and the diagnosing section is configured to determine whether the gas sensor is in the improper condition or not, by comparing, with a fourth threshold level, an average of extreme values when the number of non-extreme values reaches a second predetermined number.

* * * * *